(12) United States Patent
Schuck et al.

(10) Patent No.: US 11,250,946 B2
(45) Date of Patent: Feb. 15, 2022

(54) SYSTEMS AND METHODS FOR AUTOMATED ROUTE CALCULATION AND DYNAMIC ROUTE UPDATING

(71) Applicant: TeleTracking Technologies, Inc., Pittsburgh, PA (US)

(72) Inventors: Joseph C. Schuck, McMurray, PA (US); Chelsie M. Hall, Pittsburgh, PA (US)

(73) Assignee: TeleTracking Technologies, Inc., Pittsburgh, PA (US)

(*) Notice: Subject to any disclaimer, the term of this patent is extended or adjusted under 35 U.S.C. 154(b) by 661 days.

(21) Appl. No.: 15/292,797

(22) Filed: Oct. 13, 2016

(65) Prior Publication Data

US 2018/0107797 A1 Apr. 19, 2018
US 2019/0155990 A9 May 23, 2019

Related U.S. Application Data

(60) Provisional application No. 62/240,753, filed on Oct. 13, 2015.

(51) Int. Cl.
*G16H 40/20* (2018.01)
*G16H 40/63* (2018.01)
(Continued)

(52) U.S. Cl.
CPC .......... *G16H 40/20* (2018.01); *G06F 16/245* (2019.01); *G16H 40/63* (2018.01); *G16H 50/20* (2018.01)

(58) Field of Classification Search
CPC ........ G16H 40/20; G16H 50/20; G16H 40/63; G06F 16/245
(Continued)

(56) References Cited

U.S. PATENT DOCUMENTS

| 7,925,603 B1* | 4/2011 | Laidig | G06Q 10/04 706/45 |
| 2007/0233534 A1* | 10/2007 | Martin | G06Q 10/06 705/301 |

(Continued)

OTHER PUBLICATIONS

European Search Report issued by the European Patent Office dated Jan. 26, 2017, for European Application 16193825.3-1958 (8 pages).

*Primary Examiner* — Robert A Sorey
*Assistant Examiner* — Kimberly A. Sass
(74) *Attorney, Agent, or Firm* — Ference & Associates LLC

(57) ABSTRACT

Systems and methods are provided for automated routing in a facility. A system may comprise at least one processor, and a storage medium comprising executable instructions to configure the processor to receive first data associated with a condition of an individual, search a database in communication with the at least one processor to identify second data for a set of milestones associated with the condition, select, based on the set of milestones, a plurality of locations in the facility corresponding to the set of milestones, receive, from the database, third data associated with performance metrics of the plurality of locations, determine a sequence of the set of milestones and a path through the plurality of locations, the path being determined by correlating the performance metrics to milestones in the set of milestones, and generate for display a graphical user interface illustrating the determined sequence and determined path.

19 Claims, 16 Drawing Sheets

(51) Int. Cl.
*G06F 16/245* (2019.01)
*G16H 50/20* (2018.01)

(58) Field of Classification Search
USPC .............................................. 705/2
See application file for complete search history.

(56) References Cited

U.S. PATENT DOCUMENTS

| | | |
|---|---|---|
| 2009/0204434 A1 | 8/2009 | Breazeale, Jr. |
| 2010/0260393 A1* | 10/2010 | Truyen ................... G16H 30/20 382/128 |
| 2011/0077958 A1 | 3/2011 | Breitenstein et al. |
| 2011/0205061 A1* | 8/2011 | Wilson ................ G05B 19/042 340/573.1 |
| 2012/0035945 A1 | 2/2012 | Jain et al. |
| 2012/0265575 A1* | 10/2012 | Torii ................ G06Q 10/06311 705/7.15 |
| 2013/0282391 A1* | 10/2013 | Easterhaus ............. G16H 40/20 705/2 |
| 2014/0108034 A1 | 4/2014 | Akbay et al. |
| 2015/0134350 A1* | 5/2015 | Lacy ..................... G06Q 10/06 705/2 |
| 2015/0178451 A1* | 6/2015 | Wallace ................ G16H 40/20 705/2 |

* cited by examiner

600

Dynamic Patient Itinerary

| Task # and Task | Predecessor | Lead Lag | Duration Optimistic | Duration Expected | Duration Pessimistic | Sim Value | EST | EFT | LST | LFT | Slack | Crit Path | Prob on CP |
|---|---|---|---|---|---|---|---|---|---|---|---|---|---|
| Start | | | | | | 0 | 0 | 0 | 0 | 0 | 0 | | |
| 1 ED | Start FS | | 10 | 15 | 20 | 14 | 0 | 14 | 0 | 14 | 0 | 1 | 0.40 |
| 2 Triage | 1 FS | -5 | 15 | 20 | 22 | 16 | 9 | 25 | 9 | 25 | 0 | 1 | 0.40 |
| 3 Consent | 2 FS | | 21 | 26 | 30 | 24 | 25 | 49 | 30 | 53 | 4 | 0 | 0.10 |
| 4 Consent2 | 2 SS | 10 | 15 | 18 | 23 | 19 | 19 | 38 | 19 | 38 | 0 | 1 | 0.30 |
| 5 DRG | 4 FS | | 13 | 15 | 17 | 15 | 38 | 53 | 38 | 53 | 0 | 1 | 0.30 |
| 6 TransportA | 3,5 FS | | 30 | 38 | 45 | 39 | 53 | 92 | 53 | 92 | 0 | 1 | 0.40 |
| 7 DiagA | 6 FS | -5 | 20 | 25 | 30 | 25 | 87 | 112 | 87 | 113 | 0 | 1 | 0.10 |
| 8 DiagB | 6 FS | 5 | 10 | 15 | 20 | 15 | 97 | 113 | 97 | 113 | 0 | 1 | 0.30 |
| 9 DiagC | 6 SS | 20 | 11 | 18 | 22 | 17 | 73 | 90 | 96 | 113 | 23 | 0 | 0.00 |
| 10 TransportC | 7,8,9 FS | | 23 | 30 | 45 | 42 | 113 | 155 | 113 | 155 | 0 | 1 | 0.40 |
| 11 PreOp1 | 10 FS | | 22 | 28 | 39 | 28 | 160 | 188 | 160 | 188 | 0 | 1 | 0.40 |
| 12 Transfer Center | FS | | 120 | 140 | 180 | 145 | 0 | 145 | -1 | 146 | 1 | 0 | 0.60 |
| 13 Admin | 12 FS | -5 | 13 | 18 | 22 | 16 | 140 | 156 | 141 | 157 | 1 | 0 | 0.60 |
| 14 TransportB | 13 SS | 10 | 15 | 20 | 25 | 21 | 150 | 171 | 151 | 172 | 1 | 0 | 0.60 |
| 15 PreOp2 | 14 FS | | 10 | 15 | 20 | 17 | 171 | 188 | 172 | 188 | 1 | 0 | 0.60 |
| 16 OR | 11, 15 FS | | 30 | 33 | 60 | 35 | 188 | 223 | 188 | 223 | 0 | 1 | 1.00 |
| 17 PACU | 16 FS | | 5 | 8 | 11 | 7 | 223 | 229 | 223 | 229 | 0 | 1 | 1.00 |
| 18 MedSurg | 17 FS | | 10 | 15 | 25 | 11 | 229 | 240 | 236 | 247 | 6 | 0 | 0.20 |
| 19 Recovery | 17 FS | | 13 | 17 | 19 | 17 | 229 | 247 | 229 | 247 | 0 | 1 | 0.80 |
| 20 Discharge | 18, 19 FS | | 20 | 25 | 45 | 29 | 247 | 276 | 247 | 276 | 0 | 1 | 1.00 |
| | | | | | | | 276 | 276 | 276 | 276 | 0 | | |

1=yes 0=no

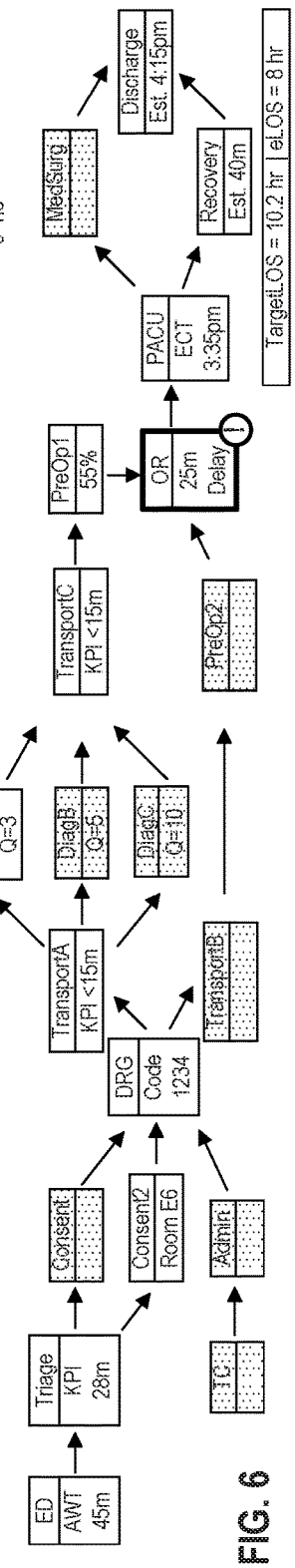

FIG. 6

Dynamic Patient Itinerary

| Task # and Task | Predecessor | Lead Lag | Duration Optimistic | Duration Expected | Duration Pessimistic | Sim Value | EST | EFT | LST | LFT | Slack | Crit Path | Prob.on CP |
|---|---|---|---|---|---|---|---|---|---|---|---|---|---|
| Start | | | | | | 0 | 0 | 0 | 0 | 0 | 0 | | |
| 1 ED | Start FS | | 10 | 15 | 20 | 15 | 0 | 15 | 0 | 15 | 0 | 1 | 0.46 |
| 2 Triage | 1 FS | -5 | 15 | 20 | 22 | 19 | 10 | 29 | 10 | 29 | 0 | 1 | 0.46 |
| 3 Consent | 2 FS | | 21 | 26 | 30 | 25 | 29 | 54 | 30 | 55 | 1 | 0 | 0.22 |
| 4 Consent2 | 2 SS | 10 | 15 | 18 | 23 | 20 | 29 | 39 | 20 | 39 | 0 | 1 | 0.24 |
| 5 DRG | 4 FS | | 13 | 15 | 17 | 16 | 39 | 55 | 39 | 55 | 0 | 1 | 0.24 |
| 6 TransportA | 3,5 FS | | 30 | 38 | 45 | 39 | 55 | 94 | 55 | 94 | 0 | 1 | 0.46 |
| 7 DiagA | 6 FS | -5 | 20 | 25 | 30 | 23 | 89 | 113 | 92 | 115 | 2 | 0 | 0.24 |
| 8 DiagB | 6 FS | 5 | 10 | 15 | 20 | 15 | 99 | 115 | 99 | 115 | 0 | 1 | 0.22 |
| 9 DiagC | 6 SS | 20 | 11 | 18 | 22 | 18 | 75 | 93 | 97 | 115 | 21 | 0 | 0.00 |
| 10 TransportC | 7,8,9 FS | | 23 | 30 | 45 | 25 | 115 | 140 | 115 | 140 | 0 | 1 | 0.46 |
| 11 PreOp1 | 10 FS | | 22 | 28 | 39 | 37 | 145 | 182 | 145 | 182 | 0 | 1 | 0.46 |
| 12 Transfer Cent | Start FS | | 120 | 140 | 180 | 137 | 0 | 137 | 2 | 139 | 2 | 0 | 0.54 |
| 13 Admin | 12 FS | -5 | 13 | 18 | 22 | 19 | 132 | 151 | 134 | 153 | 2 | 0 | 0.54 |
| 14 TransportB | 13 SS | 10 | 15 | 20 | 25 | 23 | 142 | 165 | 144 | 167 | 2 | 0 | 0.54 |
| 15 PreOp2 | 14 FS | | 10 | 15 | 20 | 15 | 165 | 180 | 167 | 182 | 2 | 0 | 0.54 |
| 16 OR | 11,15 FS | | 30 | 33 | 60 | 53 | 182 | 235 | 182 | 235 | 0 | 1 | 100 |
| 17 PACU | 16 FS | | 5 | 8 | 11 | 7 | 235 | 242 | 235 | 242 | 0 | 1 | 100 |
| 18 MedSurg | 17 FS | | 10 | 15 | 25 | 17 | 242 | 259 | 242 | 259 | 0 | 1 | 0.49 |
| 19 Recovery | 17 FS | | 13 | 17 | 19 | 16 | 242 | 258 | 243 | 259 | 1 | 0 | 0.51 |
| 20 Discharge | 18,19 FS | | 20 | 25 | 45 | 35 | 259 | 294 | 259 | 294 | 0 | 1 | 100 |
| | | | | | | | 294 | 294 | 294 | 294 | | | |

1=yes 0=no

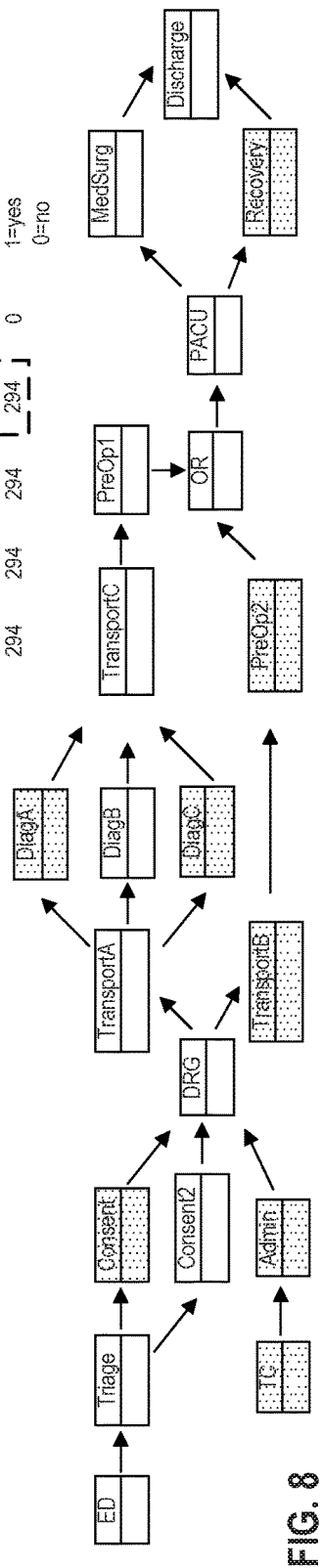

FIG. 8

M, Nancy
DOB 2/11/70
C-Diff Non-critical

(T) (ISO) (EMTALA)

Case Status Active

| | Sending Facility | Sending Physician | Receiving Facility | Receiving Physician |

General Hospital
Cardiology Unit
123-345-4566

Dr. K
Cardiology Unit
555-333-0294

Hospital East
Cardiology Unit
777-222-1111

Dr. J
Cardiology Unit
777-222-1112

▎1

/ Edit

Community Health System
Recommended Milestones:

Diagnosis: X

| Lab Y | Lab Z | Operation Y Evaluation | Medication A | Medication B |

Projected LOS: 5 days    LOS To-Date: 3 days

| Jobs | Employees | Administration | | | | | | | | Welcome, SuperUser \| Help \| Log Out |
|---|---|---|---|---|---|---|---|---|---|---|

Jobs

Search 🔍   Filter By [All Statuses ▶]   [Last 30 Days ▶]   Show [23 ▶]   ▼Prev [1 ▶] of 8 Next ▲   ⊕ Create Job 200 Results

| Created ▶ | Status | Job ID | Task ▶ | Qty | Priority | Requesting Dept | Origin | Location/Destination |
|---|---|---|---|---|---|---|---|---|
| 6:03 PM | Assigned | 140916 | Heart Monitor | 3 | Critical | 5 West | Central Supplies | 5 West -- Rm 539 |
| 6:01 PM | Assigned | 140915 | IV Pole | 19 | Critical | 9 East ICU | Central Supplies | 5 West -- Rm 539 |
| 4:23 PM | Pending | 140914 | Infusion Pump | 1 | Medium | 9 East ICU | 9 East Hallway | Central Supplies |
| 4:16 PM | Pending | 140913 | A/C Repair | -- | High | NICU 5 | -- | NICU 5 |
| 3:34 PM | Dispatched | 140912 | Room Too Hot | -- | Medium | Unit 72 | -- | Room 281 |
| 11:54 AM | In Progress | 140911 | Bring New Linens | 2 | Low | 2 North | Linen | 2 North -- Rm 33 |

Assigned To   Requested By   Occurs
Jim Henry x 63456   John Doe x 64567   Every Tuesday starting 05/20/2014 at 5:00 PM
                                       No end date.                              [View Job Details]

| Mon 10:33 PM | Assigned | 140910 | Deliver Dinner | 1 | Medium | 3 East | Food Services | 3 East -- Rm 8 |
| Mon 20:22 PM | Assigned | 14099 | Trash Pickup | -- | Low | Cafeteria | -- | Cafeteria |
| Sun 11:52 PM | Suspended | 14098 | Vandalism Repair | -- | Low | Cafeteria | -- | Cafeteria |
| Sun 10:35 PM | Delayed | 14097 | Bariatric Bed | 1 | High | 9 North | Central Supplies | 9 North |
| Sun 5:31 AM | Completed | 14096 | Outlet Repair | -- | Critical | NICU 5 | -- | NICU 5 -- Rm 502 |
| Sat 11:35 PM | Completed | 14095 | Ceiling Leak | -- | Critical | ER Entrance | -- | ER Entrance |
| Sat 10:44 PM | Canceled | 14094 | Lightbulb Change | -- | Low | Food Services | -- | Food Court |
| Sat 3:45 PM | Suspended | 14093 | A/C Replacement | -- | Medium | 5 West | -- | 5 West -- Rm 503 |
| Sat 11:23 AM | Completed | 14092 | Cabinet Repair | -- | Medium | 7 East | -- | 7 East -- Rm 700 |
| Sat 8:59 AM | Completed | 14091 | IV Pump | 1 | High | 7 East | Central Supplies | 7 East -- Rm 709 |

Show [23 ▶]   ▼Prev [1 ▶] of 8 Next ▲

Employees

Search 🔍
Filter By [All Statuses ▶]

| John Adams | Available |
| | Completed 2 of 2 |
| Peter Best | Available |
| | Completed 1 of 3 |
| Stevie Griffin | Available |
| | Completed 0 of 3 |
| John Henry | In Progress |
| | Completed 2 of 3 |
| Owen Johnston | Dispatched |
| | Completed 2 of 3 |
| Joel Franklin | Available |
| | Completed 2 of 2 |
| Andy Kline | Break |
| | Completed 3 of 3 |
| Tom Kingston | Delayed |
| | Completed 2 of 9 |
| Aleta Giuliani | Available |
| | Completed 4 of 7 |
| Dan Attica | Available |
| | Completed 2 of 6 |
| Homer Clemens | Break |
| | Completed 3 of 6 |
| Peter Pan | Break |
| | Completed 0 of 0 |

FIG. 11

SYSTEMS AND METHODS FOR AUTOMATED ROUTE CALCULATION AND DYNAMIC ROUTE UPDATING

BACKGROUND

Modern health care facilities have highly skilled personnel, high-tech patient monitoring systems, communication systems, and in some instances, patient and equipment location tracking systems. Despite the high-tech environment, these facilities still fail to capitalize on the technology and data generated within the facility and determine the most effective routes and paths for patients through the facility during their stay. Often times, cross-talk between communication and scheduling systems in different departments of the facility is non-existent, and patient paths through milestones or locations in the facility are uncoordinated. Traditional scheduling systems also create bottlenecks in certain areas of the facility due to a lack of real-time census and predictive data about other departments.

In view of the problems discussed above, improved systems and methods for automated patient routing are needed.

SUMMARY

Disclosed embodiments relate to computerized systems and methods for automated routing and route management. In some embodiments, the computerized systems and methods generate patient itineraries specifying the events and milestones for the patient's stay in the facility based on their condition. The automated system determines a sequence of the events/milestones, and a path through the sequence of events and locations in the facility associated with the events, to provide a route that effectively incorporates real-time performance metrics of the different hospital units (locations) in the facility. The disclosed systems also enable automated scheduling and electronic message generation based on the determined paths and event sequences, to enable effective cross-talk between computer systems in the facility and provide scheduling based on performance metrics of the locations.

Itinerary creation may be based on data received about the patient, such as patient condition and patient characteristics, in combination with real-time and historical data associated with hospital department wait time trends, established procedures, department and personnel schedules. Disclosed embodiments may utilize any performance metrics and data that may affect the length of a patient stay and quality of care. The created itinerary may include one or more aspects of patient care from the time they are admitted to the moment they are discharged, such as a treatment schedule, a testing schedule, an examination or checkup schedule, hospital locations for each scheduled item, a caregiver or personnel assigned to each scheduled item, and equipment/medicine/lab supplies required for each scheduled item.

Itinerary management may include monitoring a status of patient care relative to the implemented itinerary. For example, a system may determine where the patient is located in the hospital at all times, whether the patient is experiencing or may experience delays in any scheduled itinerary items, and the possible "detours" to avoid any further delays. In some embodiments, itinerary management may include automated recalculation and implementation of an altered patient itinerary. The altered patient itinerary may trigger the deletion of job tasks associated with the original itinerary, and the creation of new job tasks associated with the altered itinerary.

In some embodiments, itinerary creation and automated management rely upon one or more of the computer networks, communication systems, personnel mobile devices, and tracking/locating systems in the hospital. Indeed, the disclosed embodiments address deficiencies in hospital computer systems, and provide improvements in hospital computer systems using a combination of current hospital computer components, coupled with new types of servers and/or specialized computer systems programmed with one or more models or algorithms for implementing methods and functions disclosed herein. In some embodiments, a centralized server or computing system compiles real-time data related to the operations of the hospital and the status of the patient, analyzes data trends and employs predictive algorithms to identify potential inefficiencies in a patient's itinerary. In some embodiments, the computing system may propose or automatically implement one or more alternative care itineraries that address one or more of the inefficiencies, without compromising the quality of care for the patient.

Consistent with the present embodiments, a computerized system for automated routing in a facility is disclosed. The system may comprise at least one processor in communication with a communications network, and a storage medium storing instructions. When executed, the stored instructions configure the at least one processor to receive first data associated with a condition of an individual, search a database in communication with the at least one processor to identify second data for a set of milestones associated with the condition, and select, based on the set of milestones, a plurality of locations in the facility corresponding to the set of milestones. The at least one processor also receives, from the database, third data associated with performance metrics of the plurality of locations, and determines, based on the first data, second data, and third data: a sequence of the set of milestones; and a path through the plurality of locations, wherein the path is determined by correlating the performance metrics to milestones in the set of milestones. The at least one processor is further configured to generate for display a graphical user interface illustrating the determined sequence and determined path.

Consistent with the present embodiments, a method for automated routing in a facility is disclosed. The method may comprise receiving, by at least one processor, first data associated with a condition of an individual, searching a database in communication with the at least one processor to identify second data for a set of milestones associated with the condition, selecting, based on the set of milestones, a plurality of locations in the facility corresponding to the set of milestones, and receiving, by the at least one processor from the database, third data for performance metrics of the plurality of locations. The method may also include determining, based on the first data, second data, and third data: a sequence of the set of milestones; and a path through the plurality of locations, wherein the path is determined by correlating the performance metrics to milestones in the set of milestones, and generating, by the at least one processor, a graphical user interface illustrating the determined sequence and determined path.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments and, together with the description, serve to explain the disclosed principles. In the drawings:

FIGS. 6-9 are examples of dynamic patient itinerary interfaces, consistent with embodiments of the present disclosure.

FIG. 10 is an example of a patient itinerary card interface, consistent with embodiments of the present disclosure.

FIG. 11 is an example of a patient itinerary administration interface, consistent with embodiments of the present disclosure.

DETAILED DESCRIPTION OF EXEMPLARY EMBODIMENTS

Reference will now be made in detail to exemplary embodiments, examples of which are illustrated in the accompanying drawing and disclosed herein. Wherever convenient, the same reference numbers will be used throughout the drawings to refer to the same or like parts.

Figure 1:
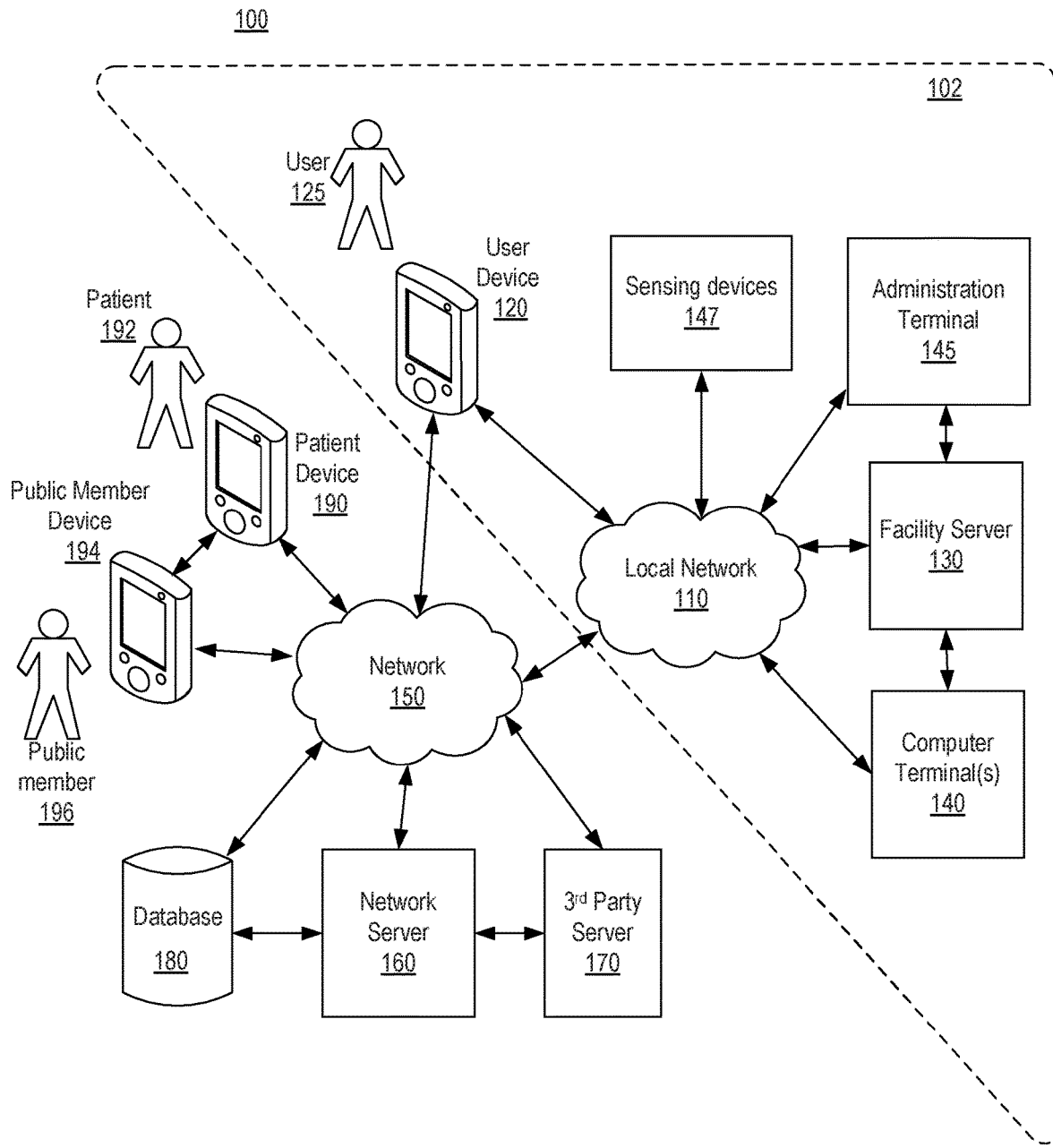
FIG. 1 depicts an example of a system environment for tracking patients within an organization, consistent with embodiments of the present disclosure.

FIG. 1 shows a diagram of a computer system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, system 100 may include a facility server 130, a computer terminal 140, an administration terminal 145, a user device 120, network server 160, third party server 170, and database 180. The components of system 100 may communicate directly, through network 150, through local network 110, or through a combination of communications methods. In some embodiments, local network 110, facility server 130, computer terminal 140, administrator terminal 145, and user device 120 may be physically disposed within a facility such as a medical facility such as a hospital or office building (i.e. as facility system 102) while network 150, network server 160, third party server 170, and database 180 may be external to the medical facility. Other components known to one of ordinary skill in the art may be included in system 100 to perform tasks consistent with the disclosed embodiments. For example, in some embodiments, facility system 102 may include one or more sensor devices such as sensors 147 located throughout the facility to monitor one or more conditions such as occupancy, temperature, humidity, proximity, and other parameters indicative of a status or condition of a room, area, equipment, or supplies. In some embodiments, sensors 147 may be disposed throughout one or more areas of a hospital as part of a security system or a real-time locating system. Additionally, in some embodiments facility system 102 may include one or more wireless receivers (not shown) configured to detect one or more wireless sensor or locating tags, to track a location of a tagged item and/or person, or a condition about the tagged item and/or person.

Computer terminal 140 may be a standalone device disposed in an office, a room, an employee station, or an alternative central location in a workplace. In some embodiments, computer terminal 140 may be a desktop or notebook computer, a flat panel or projected display, touch screen monitor, or any other display. In some embodiments, computer terminal 140 may be associated with a particular room in a facility, such as a particular patient room, hotel room, conference room, or any other type of room. Thus, a message or task request received from a computer terminal 140 may automatically associate the task request or message with the room in which computer terminal 140 is installed.

Administrator terminal 145 may include a computer system or device associated with a user 125 that manages or oversees a portion of facility system 102. For example, administrator terminal 145 may comprise a computer system located at a head nurse station, a housekeeping manager's office, or any other department manager's office or station.

User 125 may be an employee in a workplace environment such as a physician, nurse, a technician, supervisor, manager, support personnel, dispatcher, or any other individual involved with the care of a patient. User 125 may operate computer terminal 140, user device 120, and/or another computer (not shown) to interact with system 100. System 100 may include multiple types of users such as, for example, caregivers, technicians, task requestors, dispatchers, and responders. Task requestors may include one or more individuals who initiate a request for a certain task to be completed, such as a nurse requesting a hospital bed. In some embodiments, dispatchers may include individuals who perform one or more tasks related to assigning requested tasks. In some embodiments, responders may include one or more individuals assigned to the requested tasks, who perform and complete the tasks.

User device 120 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, user device 120 may be a computer system or mobile computer device that is operated by user 125. In some embodiments, user device 120 may be associated with a particular individual such as user 125, such that task assignments directed toward user 125 are sent to mobile device 120.

In some embodiments, user device 120 may communicate with facility server 130 and/or network server 160 via direct wireless communication links (not shown), or via a combination of one or more of local network 110 and/or network 150.

In some embodiments, one or more individuals such as the patient 192 or a member of the public 196 may send and receive information to facility system 102. In the example shown, patient 192 may operate patient device 190, which may be similar in form and function to user device 120. In some embodiments, patient 192 may provide information regarding location, symptoms, ratings for satisfaction of care, indication of delay, and any other information relevant to a patient diagnosis, or treatment protocol and itinerary.

Public member 196 may an individual associated with the patient who is not a hospital employee such as, for example, a primary care physician of the patient, or a relative of the patient. Public member 196 may operate public member device 194, which may be similar in form and function to devices 190 and 120.

Facility server 130 may be operated by a facility such as a hospital, business, retail location, and the like. Facility server 130 may enable communication within a computer-based system including computer system components such as desktop computers, workstations, tablets, hand held computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™, Ethernet, and other suitable short-range connections that enable computer terminal 140 and user device 120 to send and receive information between the components of system 100. In some embodiments, local network 110 may be excluded, and computer terminal 140 and user device 120 may communicate with system 100 components via network 150. In some embodiments, computer terminal 140 and/or user device 120 may communicate with one or more system 100 components via a direct wired or wireless connection. In some embodiments, local network 110 may comprise a portion of network 150 or an extension of network 150.

Network server 160, Third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service, Azure Mobile Services, or Google Cloud Messaging. In such embodiments, third party server 170 may handle the delivery of messages and notifications related to functions of the disclosed embodiments, such as task creation, task assignment, task alerts, and task completion messages and notifications.

In some embodiments, system 100 may include configurations that vary from the example shown in FIG. 1, which illustrates a facility system 102 working in concert with a cloud computing system including network server 160, third party server 170, and database 180. As a first variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and message-related functions of the disclosed embodiments.

Figure 2:
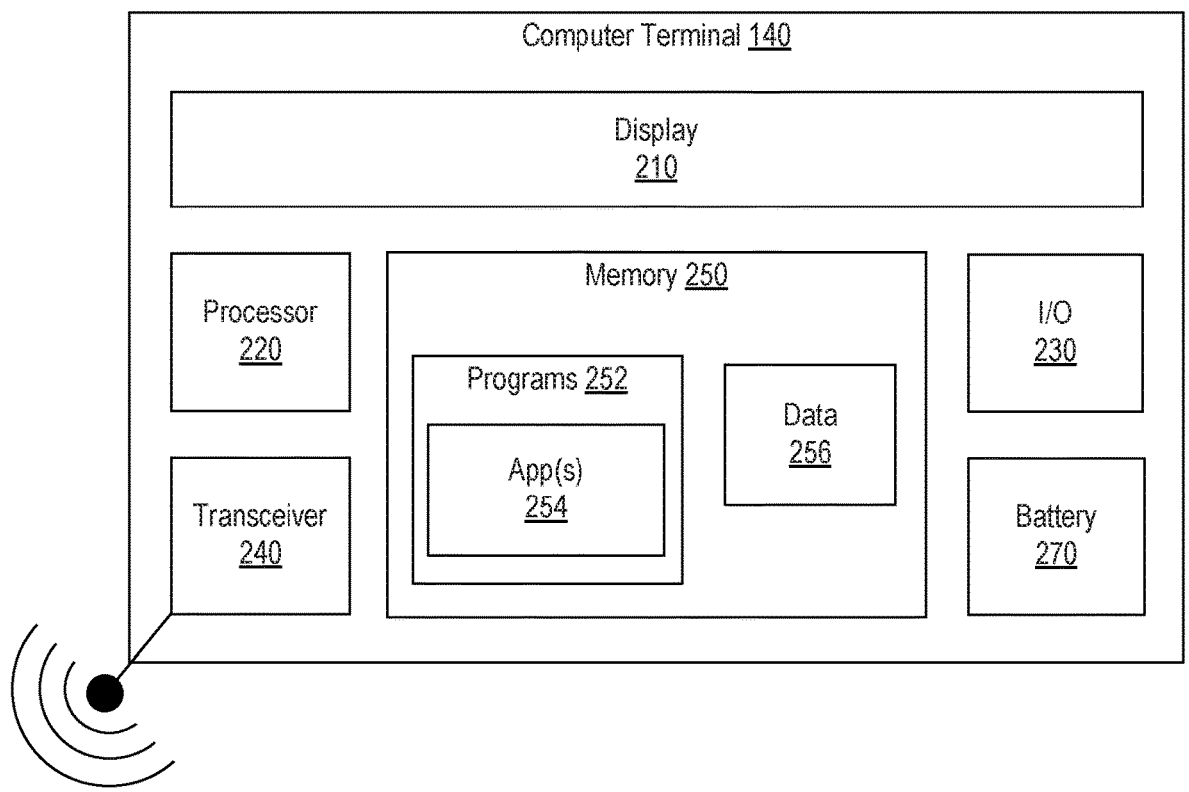
FIG. 2 depicts an example of a computer terminal, consistent with embodiments of the present disclosure.

FIG. 2 shows a diagram of computer terminal 140, consistent with disclosed embodiments. As shown, computer terminal 140 may include a display 210, one or more processors 220, input/output ("I/O") devices 230, a transceiver 240, and memory 250.

Display 210 may include one or more screens for displaying task management information such as, for example, liquid crystal display (LCD), plasma, cathode ray tube (CRT), or projected screens.

Processor 220 may be one or more known processing devices, such as microprocessors manufactured by Intel™ or AMD™ or licensed by ARM. Processor 220 may constitute a single core or multiple core processors that executes parallel processes simultaneously. For example, processor 220 may be a single core processor configured with virtual processing technologies. In certain embodiments, processor 220 may use logical processors to simultaneously execute and control multiple processes. Processor 220 may implement virtual machine technologies, or other known technologies to provide the ability to execute, control, run, manipulate, store, etc. multiple software processes, applications, programs, etc. In another embodiment, processor 220 may include a multiple-core processor arrangement (e.g., dual, quad core, etc.) configured to provide parallel processing functionalities to allow computer terminal 140 to execute multiple processes simultaneously. One of ordinary skill in the art would understand that other types of processor arrangements could be implemented that provide for the capabilities disclosed herein.

I/O devices 230 may include one or more devices that allow computer terminal 140 to receive input from a user. I/O devices 230 may include, for example, one or more pointing devices, keyboards, buttons, switches, touchscreen panels, cameras, barcode scanners, radio frequency identification (RFID) tag reader, and/or microphones.

Transceiver 240 may include one or more communication modules for establishing communication between computer terminal 140 and other devices of system 100 via, for example, local network 110 and/or network 150. For example, transceiver 240 may include circuitry and one or more antennas for communicating wirelessly with local network 110 using a short range/near-field wireless communication protocol such as Bluetooth™, Bluetooth™ LE, WiFi, and Zigbee. Further, transceiver 240 may communicate with network 150 and/or local network 110 using any known network protocol including any form of wired or wireless internet access.

Memory 250 may include a volatile or non-volatile, magnetic, semiconductor, solid-state, tape, optical, removable, non-removable, or other type of storage device or tangible (i.e., non-transitory) computer-readable medium that stores one or more program(s) 252, such as app(s) 254, and data 256. Data 256 may include, for example, user information, task information, and display settings and preferences. In some embodiments, data 256 may include one or more rule sets for prioritizing and assigning tasks to one or more employees.

Program(s) 252 may include operating systems (not shown) that perform known operating system functions when executed by one or more processors. By way of example, the operating systems may include Microsoft Windows™, Unix™, Linux™, Android™ and Apple™ operating systems, Personal Digital Assistant (PDA) type operating systems, such as Microsoft CE™, or other types of operating systems. Accordingly, disclosed embodiments may operate and function with computer systems running any type of operating system. Computer terminal 140 may also include communication software that, when executed by a processor, provides communications with network 150 and/or local network 110, such as Web browser software, tablet, or smart hand held device networking software, etc.

Program(s) 252 may also include app(s) 254, such as a patient itinerary creation and management app, which when executed causes computer terminal 140 to perform processes related to creating one or more patient itineraries, managing the created itineraries with real-time analysis and modification, and performing automated tasks related to the management of patient itineraries. For example, app(s) 254 may configure computer terminal 140 to generate and display one or more dynamic patient itinerary display and control interfaces, to provide a calculated itinerary for a patient, display a real-time status of the patient's progress through the itinerary, identify potential delays or complications in patient care, and provide one or more alternative itineraries to mitigate the delays or complications, receive instructions from one or more user 125. Furthermore, app(s) 254 may perform one or more automated tasks associated with the patient itinerary including, for example, generating one or more job tasks related to the patient itinerary based on the patient's status and progress, canceling and/or rescheduling one or more job tasks based on changes in the itinerary, requesting equipment or supplies associated with a task, and tracking the real-time status of all tasks related to the patient itinerary. In some embodiments, app(s) 254 may configure one or more computer systems to analyze historical patient itinerary data and hospital performance data to identify patterns, trends or correlative relationships in the historical data. For example, trends in historical data may indicate that certain patient diagnoses are associated with certain lengths of stay, or often experience delays and complications in certain portions of the itinerary. In some embodiments, historical data may include the events/milestones, locations, sequence(s), path(s), timestamps, and performance metrics associated with a single patient's journey, such that facility server 130 may reconstruct the entire journey/visit, and play a computer simulation of the journey/visit forward or backward in time. Historical data, identified trends and patterns, and correlative relationships may be identified through regression analysis, queuing analysis and other known statistical analysis methods, stored, and recalled during the creation and/or modification of new patient itineraries, to provide ever-improving patient care and efficiency. Correlations could be stored, retrieved and processed as Stochastic Information Packets (SIPs), Distribution Strings (DIST) or Stochastic Library Unit with Relationships Preserved (SLURPs). As discussed in further detail below, in some embodiments the implementation of these functions and the advantages realized by the present embodiments are attributed to the use of high-speed data and communication network, as well as personal communication and tracking devices disposed throughout a hospital.

Figure 3:
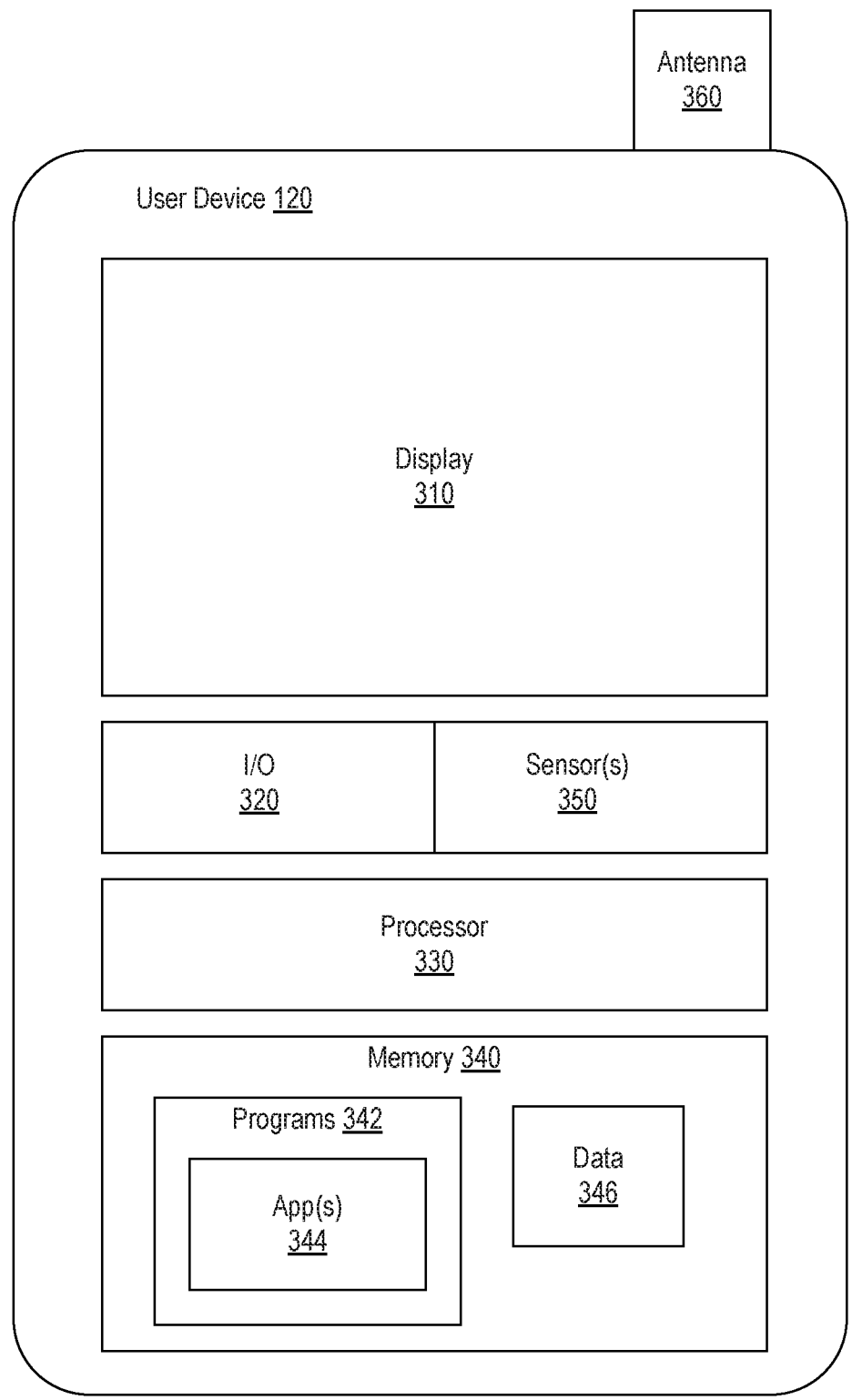
FIG. 3 depicts an example of a user device, consistent with embodiments of the present disclosure.

FIG. 3 shows a diagram of an exemplary user device 120, consistent with disclosed embodiments. As shown, user device 120 may include display 310, I/O device(s) 320, processor 330, memory 340 having stored thereon data 346 and one or more programs 342, such as app(s) 344, sensor(s) 350, and antenna 360.

Display 310 may include one or more devices for displaying information, including but not limited to, liquid crystal displays (LCD), light emitting diode (LED) screens, organic light emitting diode (OLED) screens, and other known display devices.

I/O devices 320 may include one or more devices that allow mobile device 120 to send and receive information. I/O devices 320 may include, for example, a pointing device, keyboard, buttons, switches, and/or a touchscreen panel. I/O devices 320 may also include one or more communication modules (not shown) for sending and receiving information via antenna 360 from other components in system 100 by, for example, establishing wired or wireless connectivity between mobile device 120 to local network 110, network 150, or by establishing direct wired or wireless connections between user device 120 and other components of system 100. Direct connections may include, for example, Bluetooth™, Bluetooth LE™, WiFi, near field communications (NFC), or other known communication methods which provide a medium for transmitting data between separate devices.

Processor(s) 330 may be one or more known computing devices, such as those described with respect to processor 220 in FIG. 2.

Memory 340 may be a volatile or non-volatile, magnetic, semiconductor, tape, optical, removable, non-removable, or other type of storage device or tangible (i.e., non-transitory) computer-readable medium such as those described with respect to memory 250 in FIG. 2.

In some embodiments, user device 120 may contain one or more sensors 350 for collecting environmental, movement, and/or security data. Sensors 350 may include: one or more environmental sensors such as, for example, ambient light sensors, microphones, air pressure sensors, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 330 may use data collected by sensors 350 to control or modify functions of program(s) 342.

Figure 4:
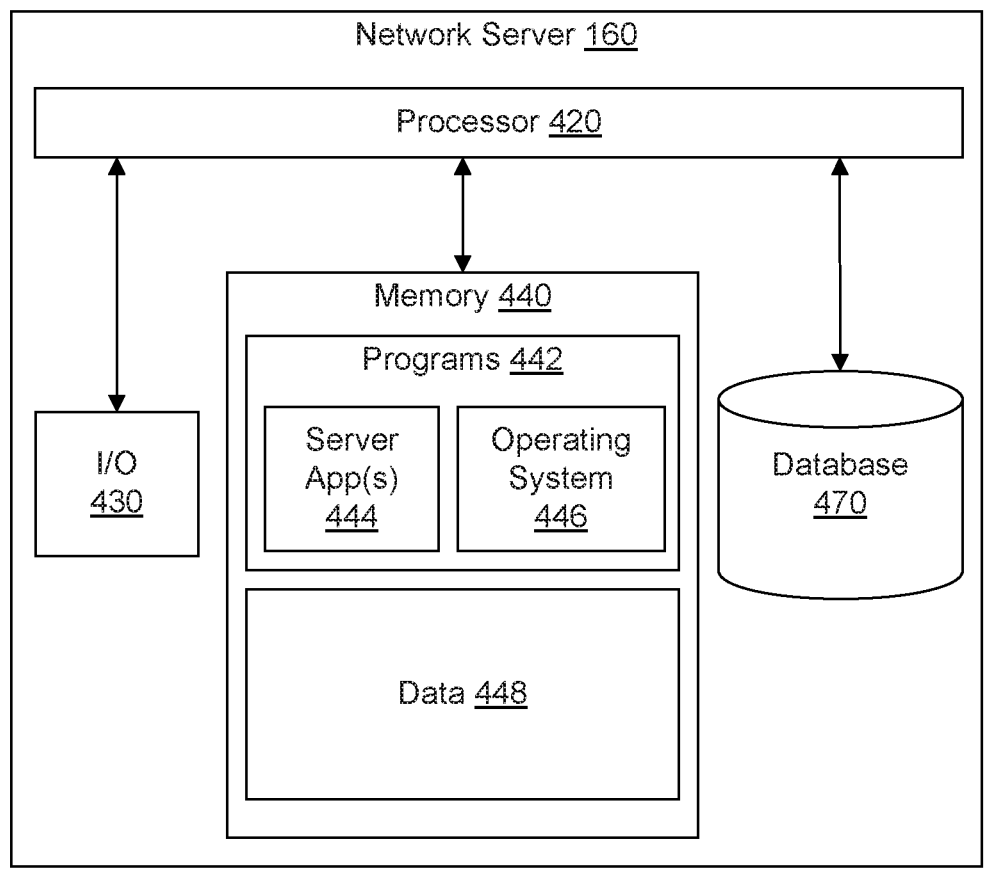
FIG. 4 depicts an example of a network server, consistent with embodiments of the present disclosure.

FIG. 4 shows a diagram of an exemplary network server 160, consistent with disclosed embodiments. In some embodiments, network server 160 may support or provide a cloud computing service, such as Microsoft Azure™ or Amazon Web Services™. In such embodiments, network server 160 may include one or more distributed computer systems capable of performing distributed computing functions and providing cloud computing services and functions consistent with disclosed embodiments. In some embodiments, network server 160 may operate in conjunction with facility server 130. In other embodiments, network server 160 may operate alone, and facility server 130 may be replaced by a network connection to network 150 and/or local network 110. In such embodiments, network server 160 may perform all functions associated with the disclosed methods. In other embodiments, facility server 130 may operate alone, without network server 160. In such embodiments, facility system 102 may operate as a standalone system, in which facility server 130 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

In some embodiments, network server 160 may connect to multiple facilities located in different geographical locations. In such embodiments, network server 160 may manage tasks that span across multiple facilities, such as a request for an equipment item to be transported between facilities. Additionally, network server 160 may collect data from multiple facilities to evaluate performance times in different facilities, and improve the accuracy of expected completion times for different types of tasks using one or more statistical/data regression algorithms.

As shown in FIG. 4, network server 160 may include one or more processor(s) 420, input/output ("I/O") devices 430, memory 440 storing programs 442 (including, for example, server app(s) 444 and operating system 446) and data 448 (including employee data 449), and a database 470. Network server 160 may be a single server or may be configured as a distributed computer system including multiple servers or computers that interoperate to perform one or more of the processes and functionalities associated with the disclosed embodiments.

Processor(s) 420 may be one or more known computing devices, such as those described with respect to processor 220 in FIG. 2.

In some embodiments, network server 160 may also include one or more I/O devices 430 including interfaces for receiving signals or input from devices and providing signals or output to one or more devices that allow data to be received and/or transmitted by network server 160. For example, network server 160 may include interface components, which may provide interfaces to one or more input devices, such as one or more keyboards, mouse devices, and the like, that enable network server 160 to receive input from one or more user 125 that is associated with facility system 102.

In some embodiments, network server 160 may include one or more storage devices configured to store information used by processor 420 (or other components) to perform certain functions related to the disclosed embodiments. In one example, network server 160 may include memory 440 that includes instructions to enable processor 420 to execute one or more applications, such as server applications, an electronic transaction application, an account status application, network communication processes, and any other type of application or software known to be available on computer systems. Alternatively or additionally, the instructions, application programs, etc. may be stored in an internal database 470 or external database 180 (shown in FIG. 1) in communication with network server 160, such as one or more database or memory accessible over network 150. Database 470 or other external storage may be a volatile or non-volatile, magnetic, semiconductor, tape, optical, removable, non-removable, or other type of storage device or tangible (i.e., non-transitory) computer-readable medium.

In one embodiment, network server 160 may include memory 440 that includes instructions that, when executed by processor 420, perform one or more processes consistent with the functionalities disclosed herein. Methods, systems, and articles of manufacture consistent with disclosed embodiments are not limited to separate programs or computers configured to perform dedicated tasks. For example, network server 160 may include memory 440 that may include one or more programs 442 to perform one or more functions of the disclosed embodiments. Moreover, processor 420 may execute one or more programs located remotely from account information display system 100. For example, network server 160 may access one or more remote programs, that, when executed, perform functions related to disclosed embodiments.

Programs 450 stored in memory 440 and executed by processor(s) 420 may include one or more server app(s) 452 and operating system 454. Server app(s) 452 may incorporate one or more apps configured to receive input of information related to tracking patient statuses such as receiving patient attributes, diagnoses, and conditions, receiving staff schedules and staff skills, receiving one or more hospital rules and legal restrictions, receiving treatment requirements, physicians' orders and regimens associated with patient diagnoses, analyzing received data using one or more rule sets, computer models, or other processing logic, generating data associated with one or more graphical user interfaces, generating one or more communications and/or commands to other computer systems or devices such as user device 120, and updating the graphical user interfaces in real-time based on new data or changes in the analysis results.

In some embodiments, memory 440 may store data 448 including data associated with patients, staff, tasks, assets such as hospital beds, assignment and graphical user interface generation algorithms, historical data, data derived from historical data such as trends, patterns, and correlative relationships. For example, data 448 may include one or more entries including employee data 449 (e.g., identifications of staff, their skill sets, their schedules and availability, staff assignment history), patient medical records, patient assignment history, data associated with patient conditions, data associated with patient treatment plans, patient bed assignments, bed availability, bed locations, bed attributes, hospital rules, established hospital procedures, calculated patient itineraries associated with patient conditions (e.g., clinical risk assessments) and diagnoses, and legal and restrictions and regulations. Data 448 may also include the current location of the patient, the status of each of the patient physician orders (e.g., lab orders, radiology orders), bed assignment priorities, milestones (e.g., clinical discharge and transfer milestones), transport request status, patient hand-off during shift change, continuity of care data for resource assignments, custom patient attributes, and the real-time statuses of delays or complications in hospital departments and units. In some embodiments, data 448 is stored in database 470, memory 440, memory 250, memory 340, database 180, and any combination thereof.

In some embodiments, memory 440 and database 470 may include one or more memory devices that store data and instructions used to perform one or more features of the disclosed embodiments. Memory 440 and database 470 may also include any combination of one or more databases controlled by memory controller devices (e.g., server(s), etc.) or software, such as document management systems, Microsoft SQL databases, Share Point databases, Oracle™ databases, Sybase™ databases, or other relational databases.

Network server 160 may communicate with one or more remote memory devices (e.g., third-party server 170 and/or database 180) through network 150 or a different network (not shown). The remote memory devices may be configured to store information and may be accessed and/or managed by network server 160. By way of example only, the remote memory devices may be document management systems, Microsoft SQL database, Share Point databases, Oracle™ databases, Sybase™ databases, or other relational databases. Systems and methods consistent with disclosed embodiments, however, are not limited to separate databases or even to the use of a database.

Figure 5:
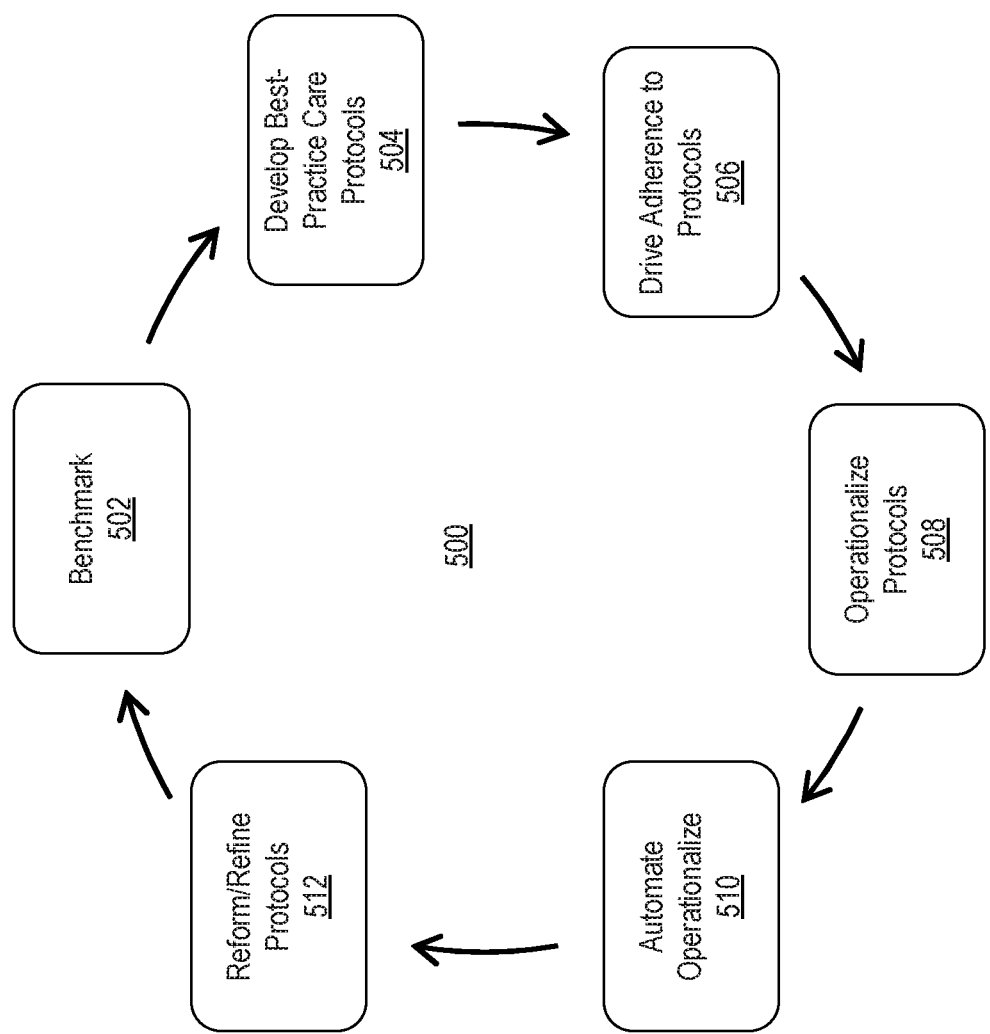
FIG. 5 depicts an example of a closed-loop flowchart for care protocol management and implementation, consistent with embodiments of the present disclosure.

FIG. 5 is an exemplary flowchart for care protocol creation, management, and implementation process 500, consistent with embodiments of the present disclosure. As shown, process 500 may include a cyclical series of steps including, for example, benchmarking performance in a hospital (or group of hospitals) 502, developing best-practice care protocols 504, driving adherence to protocols 506, operationalizing protocols 508, automating protocol operation 510, and reforming/refining protocols 512. Process 500 provides medical care facilities and medical care systems, such as hospitals and hospital systems, and/or managed care organizations with a mechanism to create care protocols, and to continuously refine protocols. Process 500 enhances the creation and refinement of efficient and effective hospital protocols by taking into account industry standard best practices for specific disease related groups, internal hospital guidelines and policies, and historical performance data specific to the hospital.

Step 502 may comprise benchmarking the performance of a hospital, group of hospitals or managed care organization. In some embodiments, benchmarking may include evaluating metrics of different departments in a hospital, or different hospitals in a heath care group. Metrics may include quantifiable and qualifible measures of efficiency and efficacy such as, for example, employee timeliness, patient backlog and scheduling congestion, treatment and care timeliness and efficacy, caregiver/staff availability and staffing levels, equipment, supply, and asset levels, hospital bed availability and wait times, transport times between hospital units, and any other measurable metric associated with operations of the medical care facility and the quality of care provided to a patient. In some embodiments, a server such as facility server 130 may compile metric data from a plurality of sources, and continuously or periodically benchmark data for the medical care facility. In some embodiments, user device 120, computer terminal 140, and/or one or more sensor devices (not shown in figures) may continuously provide metric data based on sensed conditions, scheduling information, and input by one or more user 125. In some embodiments, metric data may include historical data previously stored in database 180. Benchmarking step 502 may comprise performing one or more statistical analyses on received metric data, in order to determine the relative performance, congestion, and timeliness of different hospital units and different hospitals, as well as other comparative metrics. In some embodiments, benchmarking step 502 may measure the efficacy of operational elements on patient outcomes, such as readmission rates, mortality rates, or infection occurrences. In some embodiments, benchmarking 502 may include a comparison of performance metrics (such as efficiency, efficacy, congestion, timeliness, census, supply and demand, etc.) across different operational elements of care within the hospital and throughout a patient itinerary such as transport modes, room occupied, fixed assets encountered, time spent out of patient room). Step 502 may result in creating benchmarking data associated with different patient diagnoses, different patient characteristics, and different times of day/week/year.

In some embodiments, step 502 may include combining performance metrics with clinical diagnosis statistics received from one or more third party systems 170 such as a managed care organization, healthcare practice management company, a public database, or a government organization such as Centers for Medicare and Medicaid Services (CMS), Centers for Disease Control and Prevention (CDC), US Environmental Protection Agency (EPA), US Food and Drug Administration (FDA), omics analytics (genomics, proteomics or metabolomics) and any other organization or source of information related to patient diagnosis and care. Clinical diagnosis statistics may represent performance metrics of other hospital hospitals, and facility server 130 may evaluate created benchmarking data against the clinical diagnosis statistics to provide a measure of the hospital's clinical and financial outcomes in relation to other hospitals represented in the clinical diagnosis statistics.

In step 504, facility server 130 may generate one or more best-practice care protocols based on the results of 502. In some embodiments, step 504 may include generating one or more protocol files based on input received from one or more user 125. Protocols may include one or more points of care, which may be events such as treatment steps and milestones required to treat a particular patient diagnosis and to discharge the treated patient from the hospital. Care may occur at one or many facilities, and at a plurality of locations within the one or many facilities. At each point of care in the protocol, one or more events may be identified and stored, and the events may be ranked in order of efficiency or efficacy, based on results from step 502. In some embodiments, efficacy and efficiency may be determined based on a statistical analysis of previous patient itinerary data, to identify sequences of steps and milestones that resulted in the highest observable success rate, and having the lowest patient readmission rate or fatality rate.

In step 506, facility server 130 may identify one or more protocols that will provide the best outcomes for the patient and the hospital. In some embodiments, facility server 130 may evaluate guidelines and rules for different diagnoses received from third party server 170, and determine whether the protocols generated in step 504 adhere to the received guidelines and rules. Protocols may be ranked based on adherence in combination with efficiency and efficacy. In some embodiments, facility server 130 may provide an indication that a hospital protocol includes one or more steps or step sequences that violate the guidelines and rules. In such embodiments, facility server 130 may automatically determine a modification to the violating protocol, based on the guidelines and rules, or facility server 130 may request input from user 125.

In step 508, facility sever 130 may implement the ranked protocols, thereby "operationalizing" the protocols. The protocols may be implemented in subsequent patient itineraries, selected by facility server 130 based on a diagnosis or characteristics of an incoming patient that match a protocol. In some embodiments, database entries for the ranked protocols may include one or more tags or metadata associating the protocols with a particular condition of the patient such as a diagnosis, patient characteristic, or combination thereof. Facility server 130 may search the database entries to identify entries having metadata, tags, or other information corresponding with the individual's condition. In some embodiments, facility server 130 may generate a graphical user interface or having a list or flowchart of events including treatment milestones representing treatment steps required for treating a patient, based on the selected protocol. Patient characteristics may include, for example, a physical attribute about the patient, a mental health attribute about the patient, a personality attribute about the patient, an acuity level of the patient, and any other quantifiable or qualifible information about the patient that may assist with patient diagnosis, placement, and/or treatment. Treatment milestones may identify a task that must be performed to treat or otherwise care for the patient. In some embodiments, facility server 130 may determine one or more locations in the facility associated with each event or treatment milestone, using one or more lookup tables or rule sets associating events with facility locations. The graphical user interface may also identify one or more of a hospital unit location, employee, or equipment/asset associated with the task for the particular patient. Treatment milestones may also be associated with an estimated date/time of completion, determined based on statistical analyses of historical data for similar tasks in similar hospital units, at similar times and dates.

In step 510, facility server 510 may automate one or more events in the selected protocol. For example, upon selecting a protocol and generating a patient itinerary, facility server 510 may identify an available hospital bed and associated location that corresponds to the patient diagnosis and characteristics, automatically reserve the bed, automatically request a transporter to move the patient from their current location to the hospital bed, and automatically place equipment and asset orders for necessary machines, medicine, and supplies to the patient's room. In some embodiments, facility server 130 may automate some or all of the events in the patient itinerary, by scheduling tasks according to personnel and hospital unit schedule data, location data for each event or milestone in the itinerary protocol, employee location data, patient location data, asset and equipment location and stock level data, and any other measurable data collected by computer terminal 140, user device 120, and hospital sensor devices.

In step 512, facility server 130 may evaluate the performance of completed itinerary events, and refine protocols. For example, facility server 130 may determine that a patient having a particular condition took X hours longer to complete certain milestones than another patient having a different condition. As another example, facility server 130 may determine that a particular hospital unit experiences abnormally high congestion/census when X number of patients having a particular condition are currently admitted to the hospital. Using this performance data, facility server 130 may continue to refine protocols and determine recommended alternative selections or orders of events and locations in the stored patient itineraries. Facility server 130 may identify protocols having abnormally low efficiency by detecting patterns in patient diagnosis, time of day/week/month, and hospital unit.

Process 500 may loop to continuously, improve hospital performance, efficiency, and efficacy, using data collected from multiple devices in the hospital, and through task automation throughout hospital stays.

FIG. 6 is a first example of a dynamic patient itinerary interface 600. Interface 600 may display a table comprising a list of milestones associated with a generated patient itinerary, and one or more performance metrics for each milestone in the itinerary. The example in FIG. 6 illustrates a patient that has undergone an operation, recovery, and discharge within 24 hours of admission. The chart portion of FIG. 6 may represent back end calculations performed by facility server 130 and/or other processors in hospital system 102. In some embodiments, back end calculations may be performed by an off-premises processor such as third party server 170 including, for example, a cloud network server. Thus, the chart portion may be accessible by a system administrator via administration terminal 145, but may not appear as the main graphical user interface on user device 120 or computer terminal 140. The flowchart/diagram shown as the bottom portion of FIG. 6 may appear as a front-end graphical user interface on user device 120 and computer terminal 140, as well as any other devices within system 100 or 102 authorized to receive and display patient itineraries and task statuses such as, for example, patient device 190 and public member device 194.

Interface 600 may display information including, for example, a task number/identifier, a predecessor task or dependency, a lead lag time, and a plurality of timing metrics (illustrated in numbers of minutes). Metrics may include an optimistic duration for the task (based on high efficiency historical data), an expected duration for the task (based on average or median historical and current data), a simulation (sim) value, an earliest start time, an earliest finish time, a latest start time, and a latest finish time. In some embodiments, interface 600 may also include a slack value indicating that the task is not on the critical path of care, and an indication of whether each task is critical to the patient treatment. Finally, in some embodiments interface 600 may include a probability value that the task/step/milestone is on the Critical Path of care.

In the flowchart depicted in FIG. 6, light boxes may indicate milestones in the itinerary in the current selected itinerary path that are expected to be followed, and milestones that were followed and completed. Shaded boxes may indicate optional milestones that are not required to complete the patient's treatment, as well as alternative milestones that are not part of the current selected itinerary path. Shaded boxes may also represent milestones that were not completed during the patient stay.

One or more milestone boxes in the flowchart may provide information associated with the milestone such as, for example, an average wait time (AWT), a key performance indicator (KPI) such as a duration that is determined to be efficient, a room number, a diagnosis code, a queue number indicating the current number of patients in line at a particular hospital unit, a completion percentage, an expected or actual delay time, an estimated completion time (or estimated ready-to-move time), an estimated duration time, and an estimated discharge date/time. In the example shown in FIG. 6, the patient is admitted through the emergency department, should proceed through triage within 28 minutes to be considered efficient, is assigned to room E6 for completing consent forms, is assigned diagnosis code 1234, and is expected to be transported via TransportA in less than 15 minutes to testing unit DiagA, where there are currently 3 other patients in queue. After testing, the patient is expected to be transported within 15 minutes to pre-operation, which is in progress and 55% complete. Afterward the patient is to undergo an operation, though there is currently a 25 minute delay in the operating room, indicated via a different colored box, a highlighted or bolded box, or another indicator such as an exclamation point or other symbol. Delay information may be determined based on, for example, real-time scheduling data for the operation room, and expected cleaning and preparation times. After operation (including the current delay), the patient is expected to complete the post anesthesia care unit at 3:35 pm, is estimated to require another 40 minutes of recovery time, and then is estimated to be discharged from the hospital at 4:15 pm. In some embodiments, the estimated completion time may include a predetermined tolerance time period or percentage, such as "4:15 pm+10-30 mins." Estimated completion time (also referred to as estimated ready to move time) associated with the events or milestones enable facility server 130 to automate scheduling functions and provide automated electronic messages and notifications.

In some embodiments, interface 600 may be interactive, and selection of any box in the flowchart may trigger the display of secondary information including additional metrics, and options for modifying or changing the milestone.

In some embodiments, interface 600 may include a symbol, colored box, or other indication of the milestone that is currently in progress. Furthermore, completed and future milestones in the itinerary may be color coded or displayed differently.

In some embodiments, interface 600 may display a target/projected length of stay time determined based on the duration for each milestone and any detected delays. In some embodiments, interface 600 may also display an estimated length of stay or eLOS, and/or a running clock of the patient visit since admission. In some embodiments, interface 600 may include multiple length of stay metrics including, for example, a running clock length of stay timer, an estimated length of stay, and a reimbursable length of stay. The estimated length of stay may be calculated based on the estimated time to complete the generated patient itinerary, and any delays or modifications thereto. The reimbursable length of stay metric may account for a Major Diagnostic Category (MDC) and/or a Diagnosis-related group (DRG) associated with the patient. A reimbursable length of stay may indicate a length of stay in the hospital for which the patient will be covered by the patient's health insurance. For example, a particular diagnostic category may have an associated reimbursable length of stay of 4 days, indicating that health insurance would cover up to 4 days of care. Thus, inefficiencies in the hospital may result in time spent caring for the patient that would not be reimbursed by insurance.

In some embodiments, interface 600 may be provided to one or more users 125 via computer terminal 140, user device 120, and any other computerized device in communication with network 150 and authorized to access patient itineraries.

Figure 7:
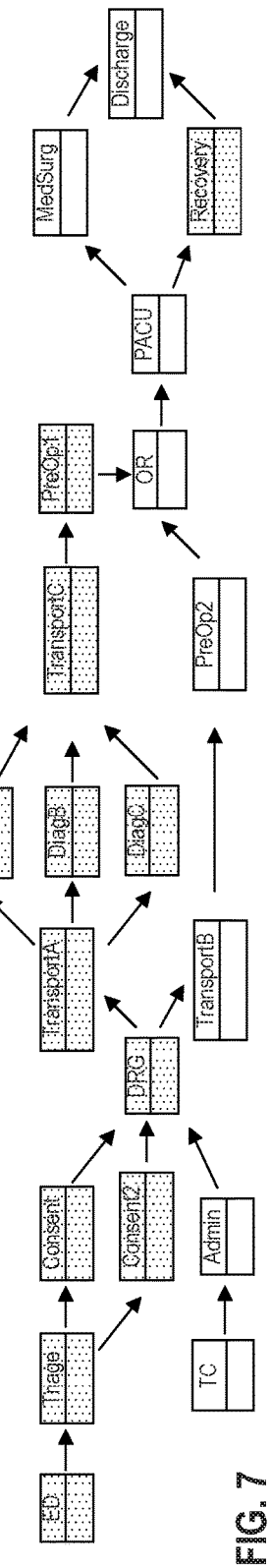

FIG. 7 is a second example of a dynamic patient itinerary interface 700. Interface 700 illustrates an example patient itinerary for a patient who has undergone elective surgery, and is admitted to the hospital.

FIG. 8 is a third example of a dynamic patient itinerary interface 800. Interface 800 illustrates an example patient itinerary for an emergency patient that undergoes an operation and is admitted to the hospital.

Figure 9:
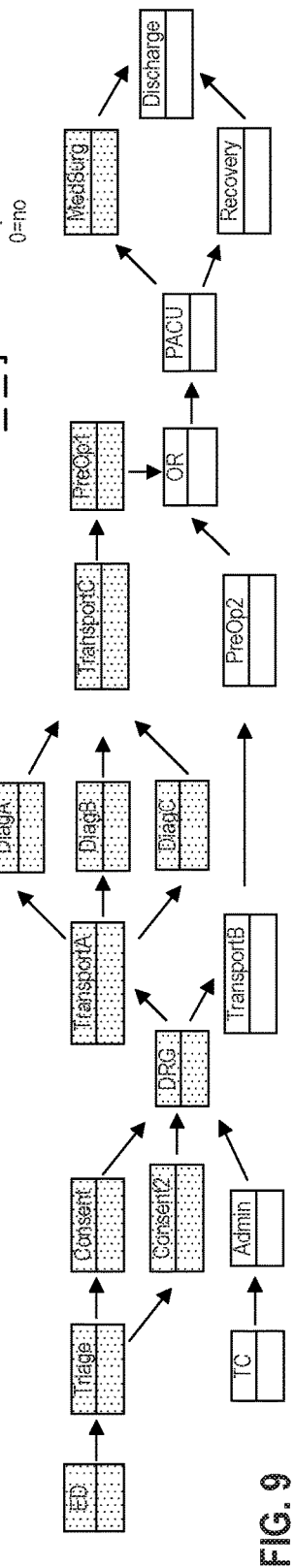

FIG. 9 is a fourth example of a dynamic patient itinerary interface 900. Interface 900 illustrates an example patient itinerary for a patient that undergoes elective surgery, and is discharged the same day.

FIG. 10 is an example of a patient itinerary card interface 1000, consistent with embodiments of the present disclosure. Interface 1000 may be presented to user 125 via any one of computer terminal 140, user device 120, and any other computer device in communication with network 150 and authorized to access patient itineraries. As shown, interface may include information about a particular patient, one or more caregivers inside and outside the hospital associated with the patient, and/or one or more icons representative of a patient diagnosis, condition, or characteristic. Interface 1000 may also include one or more icons associated with recommended milestones in the itinerary determined based on the patient diagnosis, requirements and guidelines, and hospital protocols. In some embodiments, interface 1000 may include indications for a projected length of stay (LOS). The projected LOS may be determined by facility server 130 by estimating a time to complete the sequence of milestones in the current patient itinerary, using historical data and trend data associate with the patient diagnosis group, historical timeliness data for the hospital units associated with the milestones, and current and projected timeliness data for the hospital units. Interface 1000 may also display a length of stay to-date, which may comprise a running clock that shows the elapsed time since patient admission. In some embodiments the displayed and/or projected length of stay metrics may be rendered in the graphical user interface as one or more histograms, or other type of graphical element to effectively convey the calculated values as compared to a curve of possible values and their occurrence frequencies in historical data. In some embodiments, interface 1000 may be interactive, and selection of a milestone icon may allow a user 125 such as a caregiver to select alternate milestones, if any are available as determined by facility server 130. In some embodiments, interface 1000 may incorporate real-time location or sensor data, and display information including a current location or a last known location with a time and date stamp (not shown in figure).

In some embodiments, selection of a milestone icon may allow user 125 to manually change one or more parameters about the milestone, request one or more tasks associated with the milestone, or enter progress data regarding the milestone. In some embodiments, facility server 130 may automatically generate a warning or alert to one or more users 125 if a manual change in milestones violates one or more of the guidelines/rules associated with the patient diagnosis, violates the hospital protocols, or is otherwise predicted to be an inefficient or ineffective solution based on historical data analysis and predictive algorithms.

In some embodiments, interface 1000 may notify user 125 of any milestones that require human intervention and cannot be fully automated.

FIG. 11 is an example of a patient itinerary administration interface 1100, consistent with embodiments of the present disclosure. In some embodiments, interface 1100 may provide some or all detailed events and tasks associated with the patient alongside a high-level macro view of the patient itinerary such as the flowchart interface shown in FIG. 6. In some embodiments, the high-level macro view may render the detailed view of interface 1100 with a contrasting color to enhance readability. In some embodiments, the graphical user interface may include one or more selectable filters to include or exclude details and portions of the user interface, as desired by the viewing user. Interface 1100 may allow for automation of items such as tasks or equipment/asset/supply/medicine delivery to a patient, based on the patient itinerary and hospital protocols. In some embodiments, interface 1100 may provide user 125 with a plurality of item options, and may suggest an item based on the generated patient itinerary. For example, interface 1100 may suggest bringing an extra-large wheelchair for a patient based on a characteristic of the patient, may suggest transporting the patient to an isolation-ready hospital bedroom based on a diagnosis or condition of the patient, or may suggest delivering a walker to the patient room on the day that the patient is scheduled for spinal surgery. Thus, facility server 130 may continuously monitor the progress of a patient through their patient itinerary and preemptively suggest milestones or items based on historical measures of efficiency and efficacy. Facility server 130 may automate the suggested items and milestones based on hospital policies and caregiver authorization.

Figure 12:
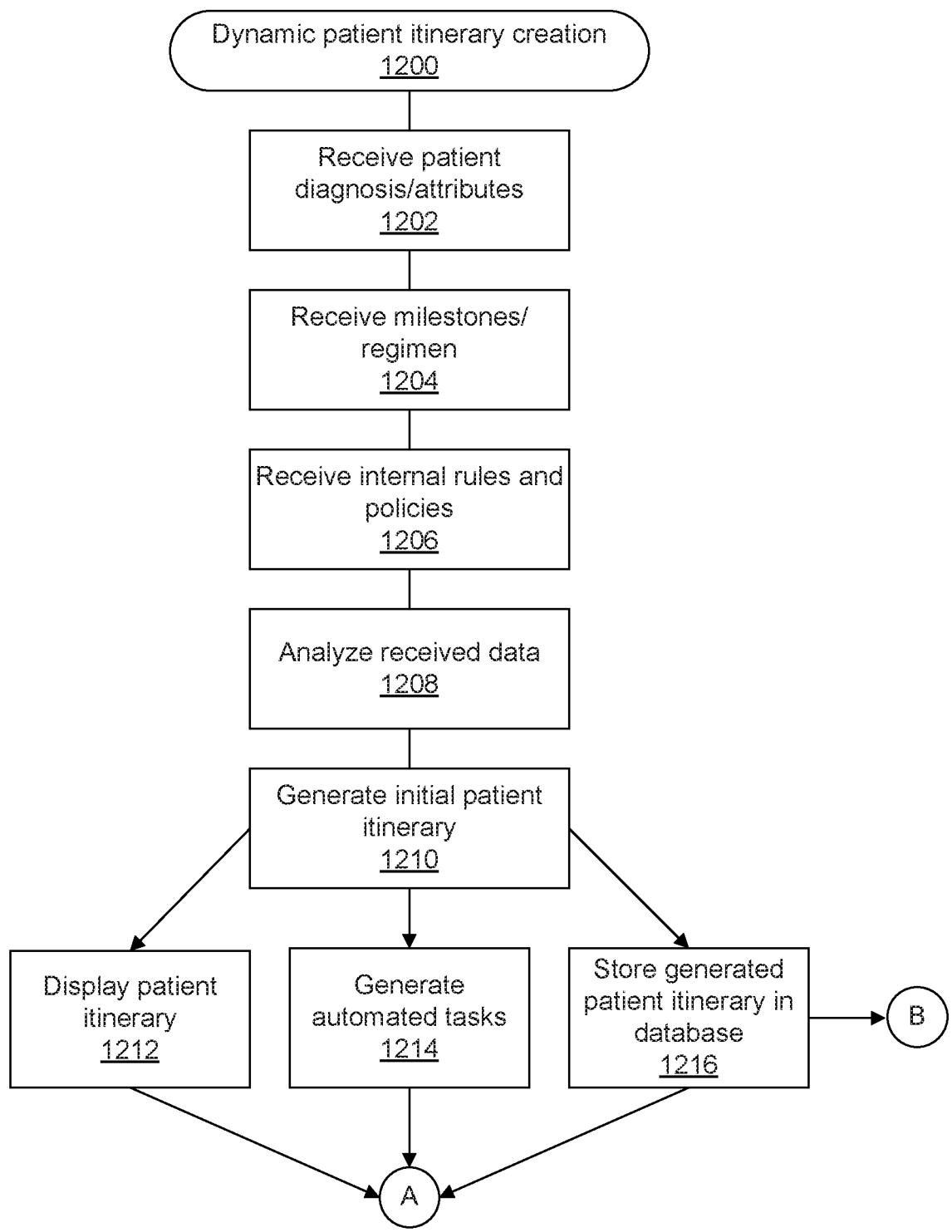
FIG. 12 is an example flowchart of a patient itinerary creation process, consistent with embodiments of the present disclosure.

FIG. 12 is an example flowchart of a patient itinerary creation process 1200, consistent with embodiments of the present disclosure. Process 1200 is described herein as being performed primarily by facility server 130. In some embodiments, however, one or more computerized devices of system 100 may perform steps of process 1200, as well as any other process disclosed herein. In some embodiments, multiple devices may perform steps of the methods disclosed herein in a distributed computing fashion.

In step 1202, facility server 130 may receive data associated with one or more patient attributes and diagnoses. In step 1204, facility sever 130 may receive data associated with one or more milestones, based on the received diagnosis and attribute data. In step 1206, facility server 130 may receive data associated with hospital rules, policies, and guidelines, as well as clinical benchmark data representing performance metrics in the hospital units and comparative performance data across multiple hospitals. In step 1208, facility server 130 may analyze received data using one or more statistical analyses.

In step 1210, facility server 130 may generate an initial patient itinerary based on the analyzed data. In some embodiments, the patient itinerary may include a proposed sequence and selection of milestones that are required or optional for completing the patient's treatment and discharging the patient. Facility server 130 may determine, based on its analysis of historical patient treatment data, best-practice data for the patient's disease-related group, and hospital data including real-time hospital unit statuses and schedule data, the most efficient treatment path through the particular hospital. In some embodiments, facility server 130 may correlate milestones identified in the itinerary with locations in the facility, and correlate performance metrics associated with the locations to determine a path through the milestones and locations that is associated with a lowest estimated completion time. In some embodiments, facility server 130 may estimate completion times for each milestone in the proposed itinerary based on historical turnaround times in combination with real-time hospital unit status information. In some embodiments, the itinerary may include one or more triggers determined based on best practice data and/or hospital procedures. For example, the itinerary may include a trigger to automate the scheduling of an MRI scan if a patient with diagnosis X does not improve after Y number of hours.

After generating the itinerary, facility server 130 may display the patient itinerary in a graphical user interface (step 1212), generate data associated with one or more automated tasks in the patient itinerary (step 1214), and generate a database entry storing the generated patient itinerary (step 1216), such as in database 180. In some embodiments, facility server 130 may provide data for displaying an interface such as the examples shown in FIGS. 6-10. The displayed interface may indicate a list of recommended milestones for the patient itinerary. Throughout steps 1210, 1212, 1214, and 1216 of process 1200, facility server 130 may store data associated with each step such as, for example, patient itinerary task lists, schedules, generated tasks, individuals associated with generated tasks, estimated completion times, estimated Ready-to-Move times (eRTM), and durations, and any other measurable and recordable data associated with the patient itineraries and tasks. Data and analyzed data may be stored, retrieved and processed as Stochastic Information Packets (SIPs), Distribution Strings (DIST) or Stochastic Library Unit with Relationships Preserved (SLURPs).

In some embodiments, the interface may indicate which milestones are completed and which are still pending. In some embodiments, facility server 130 may calculate performance metrics for each milestone in real-time, and provide those metrics for each completed milestone, and pending milestone. For example, facility server 130 may determine a performance rating for a completed milestone, to indicate how the hospital unit's timeliness compared to facility server 130's original estimated completion time.

In some embodiments, facility server 130 may generate a custom graphical user interface for different users 125 associated with the patient itinerary, depending on the particular user 125's role. For example, a transporter employee user 125 may view a graphical user interface on user device 120 that displays only a list of patients to be transported, as well as the pickup and drop-off locations, and the pickup and drop-off times. As another example, a nurse may view a graphical user interface listing the treatments and tests determined for one or more patients, based on the respective patient itineraries. In such embodiments, facility server may determine the role of each user 125 associated with a patient itinerary, and employ one or more rule sets to determine the types of data to include in the graphical user interface for each user 125. Rule sets may be predetermined and stored based on the needs of the hospital, and may also include different levels of authorization, to ensure that only authorized users 125 receive and view sensitive information about a patient, and unauthorized employee users 125 can only receive and view non-sensitive information.

Figure 13:
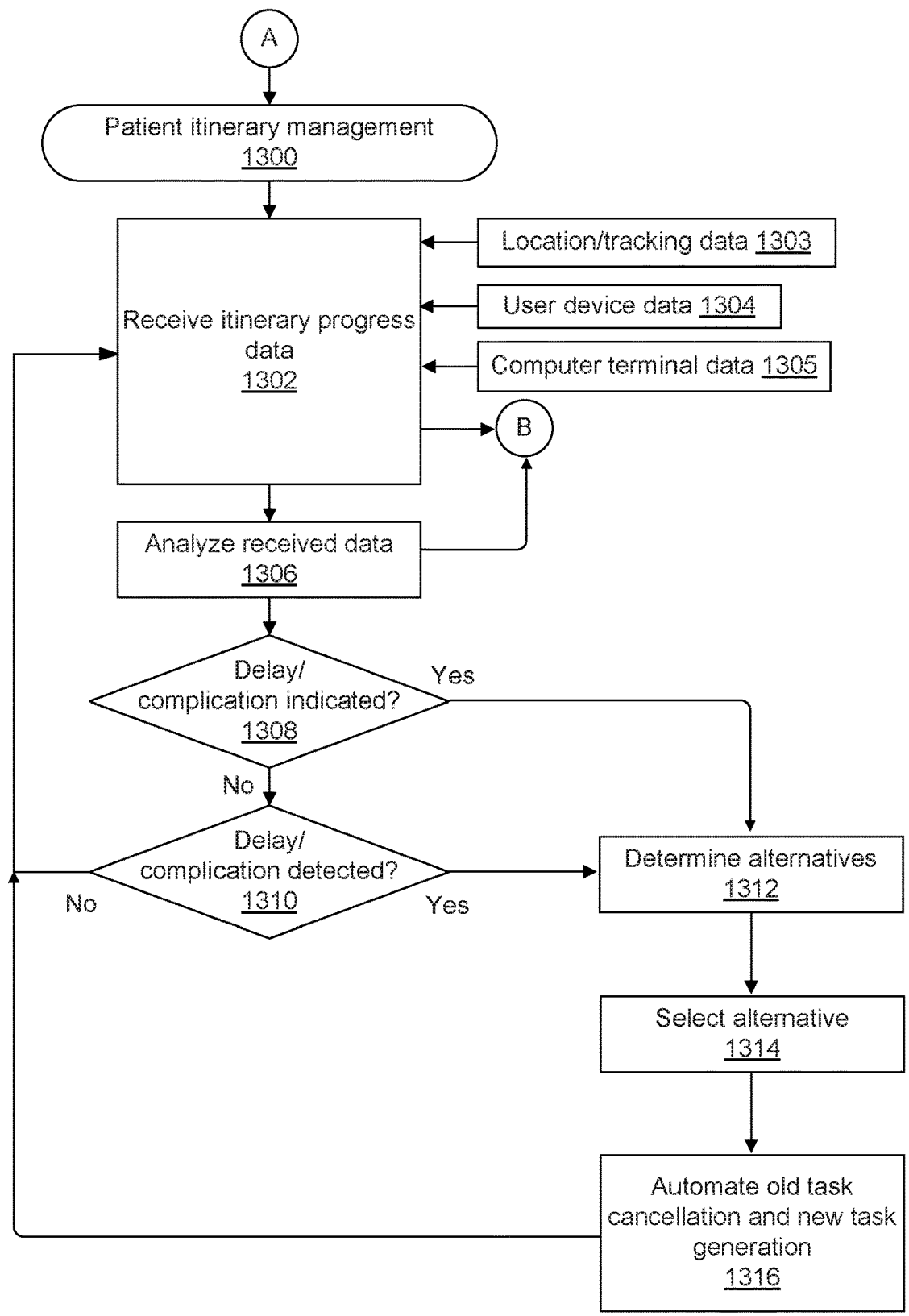
FIG. 13 is an example flowchart of a patient itinerary management process, consistent with embodiments of the present disclosure.

After completing step 1210, process 1200 may proceed to point A of process 1300 (FIG. 13).

FIG. 13 is an example flowchart of a patient itinerary management process 1300. Process 1300 may begin at point A, upon completing step 1210 in FIG. 12. In step 1302, facility server 130 may receive itinerary progress data from one or more of user device 120, computer terminal 140, and one or more sensors located throughout the hospital. In some embodiments, progress data may include an indication that a milestone task is started, in progress status, or completed. Such progress data may be entered by user 125 and transmitted to facility server 130. In some embodiments, progress data may be automatically generated by a sensing device or tracking tag. For example a real time locating system tag may provide location data indicating that the patient, an employee such as a caregiver, or an asset has arrived at its intended destination, and the time of arrival. Thus, progress data may include location/tracking data 1303, user device data 1304, and/or manually-entered computer terminal data 1305. Facility server 130 may process the received data to automatically indicate the milestone as completed, and automatically generate one or more tasks associated with the next milestone.

In step 1306, facility server 130 may analyze received data to evaluate the performance of the hospital according to the schedule and guidelines in the itinerary milestones. For example, facility server 130 may determine whether the patient itinerary is on track, experiencing a delay, suggest alternative steps/path, reorder steps or may experience a delay. In some embodiments, facility server 130 may predict or identify a deviation in an amount of time to complete task or the estimated completion time, from the originally estimated completion time. Facility server 130 may use one or more control charts to identify deviations from the original schedule and predict delays, by determining whether the estimated completion time for each task falls outside a predetermined tolerance level. For example facility server 130 may determine whether a duration of a current task falls outside a predetermined percentage or standard deviation of a mean duration for the task. In step 1308, facility server 130 may determine whether a user 125 has manually indicated that there is a delay or complication with a milestone in the itinerary. If a delay or complication is indicated ("Yes" in 1308), then process 1300 may proceed to step 1312, in which facility server 130 may recalculate milestone options for the patient to determine one or more alternative milestones. In some embodiments, facility server 130 may determine another milestone in the current itinerary that may be completed in place of the delayed milestone, without compromising efficiency or treatment efficacy. For example, in a patient itinerary requiring tests in hospital units labA and labB, labA may be experiencing severe delays. Facility server 130 may determine a real-time status of labB, and check best practice data and hospital guidelines to ensure that visiting labB before labA is an effective and efficient alternative. If so, facility server 130 may select the alternative milestone (step 1314), and automate one or more tasks based on the itinerary change (step 1316). For example, in step 1316, facility server 130 may automatically cancel a transport task associated with transporting the patient to labA, and automatically generate a new task associated with transporting the patient to labB. The automated task cancellation and generation may also include providing one or more electronic messages to users 125 associated with the itinerary change, or changing one or more graphical user interfaces on user devices 120. In some embodiments, facility server 130 may require input to authorize a particular change in itinerary. In such embodiments, facility server 130 may present options for selection by a caregiver (not shown in figure). After selecting the alternative milestone, process 1300 may return to step 1302, to continue monitoring progress data for the patient itinerary.

Returning to step 1308, if a delay or complication is not manually indicated ("No" in step 1308), then process 1300 may proceed to step 1310, in which facility server 130 may determine whether a delay or indication is detected or predicted based on analysis of the progress data. In some embodiments, facility server 130 may dynamically alter aspects of the patient itinerary based on the progress data and real-time scheduling data. For example, if facility server 130 determines that a milestone was completed behind schedule, facility server 130 may determine whether the hospital unit and/or user 125 associated with the next milestone are still available, and may assign the milestone to a different hospital unit or employee if congestion is predicted. As another example, if a milestone is falling behind schedule, and an upcoming milestone has a narrow time window, facility server 130 may determine that the milestone will not be met, by considering historical data as well as current backlogs in the relevant hospital unit. If a complication or delay is detected ("Yes" in 1310), process 1300 may again proceed to step 1312. If no complication or delay is detected, then process 1300 may return to step 1302, to continue monitoring itinerary progress.

Figure 14:
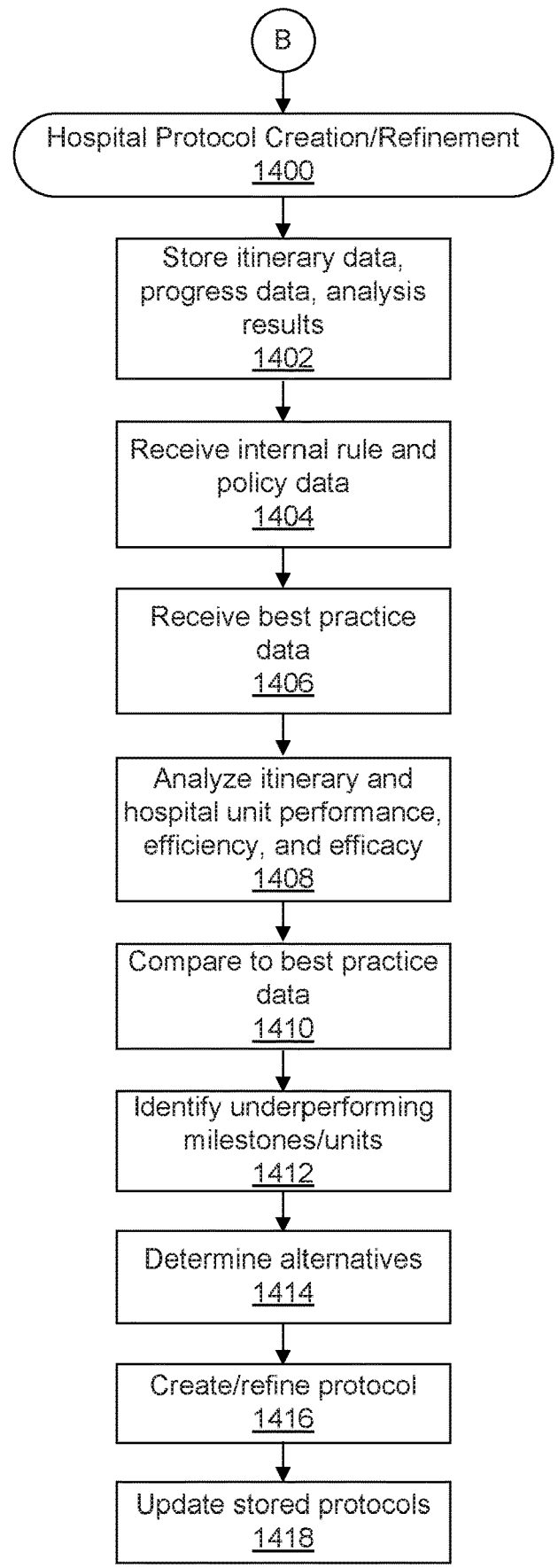
FIG. 14 is an example flowchart of a hospital protocol creation/refinement process, consistent with embodiments of the present disclosure.

FIG. 14 is an example flowchart of a hospital protocol creation/refinement process 1400. While process 1400 is illustrated as a linear sequence of events, in practice process 1400 may loop continuously and have varying orders of steps.

Process 1400 is driven by collected data, including data associated with established hospital protocols (if any), best practice data for best practices observed among various diagnosis related groups, hospital performance data, hospital scheduling data, patient itinerary data, itinerary efficiency and efficacy data, and any other collected or derived data associated with the creation and refinement of a hospital protocol. Process 1400 begins at point B, with the collection of various data from processes 1200 and 1300. For example, when a new patient itinerary is stored in a database such as database 470 or 180, the itinerary data may also be used within process 1400. Itinerary data may include, for example, a listing of milestones determined for a patient having diagnosis X and attributes Y at hospital Z. Itinerary data may also include identification of particular hospital units assigned to various milestones, employees assigned to the milestones, milestone start times and estimated completion times, equipment associated with milestones, and any other information included in the patient itinerary.

Data collected at point B may also include received and analyzed itinerary progress data, as shown in FIG. 13. Received itinerary progress data may include, for example, location and tracking data for a patient, employee, and/or equipment or asset such as a wheelchair, infusion pump, or hospital bed. Itinerary progress data may also include data received from one or more user devices 120 and computer terminals 140, including indications of task completion or complications/delays. Received itinerary progress data may also include analysis results of other received data, such as derived performance metrics associated with milestone completion efficiency, and treatment efficacy/success rates. In some embodiments, received itinerary progress data may also include data associated with one or more alternate milestones determined and selected during a patient stay, and the corresponding efficiency and efficacy metrics associated with the alternate milestone.

In step 1402, facility server 130 may store any itinerary data, progress data, and analysis results. Facility server 130 may store data in a memory or database such as database 470 or 180. In some embodiments, facility server 130 may store data at the end of every patient stay (e.g. the completion of a patient itinerary), or a continuous or scheduled/periodic basis. In some embodiments, facility server 130 may organize stored data according to different diagnosis related groups, or based on other classifications such as, for example, time of day/week/year, hospital unit, and any other category relevant to the stored data depending on the needs of the hospital. In some embodiments, facility server 130 may update one or more databases associated with Stochastic Information Packets (SIPs), Distribution Strings (DIST) or Stochastic Library Unit with Relationships Preserved (SLURPs) based on the results of each completed patient journey and the associated performance metrics.

In step 1404, facility server 130 may receive, from a networked database or memory, internal hospital rule and policy data, including hospital guidelines for care and any previously established protocols.

In step 1406, facility server 130 may receive best practice data for one or more diagnosis related groups. In some embodiments, facility server 130 may receive best practice data from one or more third party server 170 operated by an entity whose purpose is to develop effective treatment plans for different diagnosis related groups. In some embodiments, third party server 170 may include a managed care organization, healthcare practice management company, a public database, a private consortia, a research hospital or university, or a government organization such as Centers for Medicare and Medicaid Services (CMS), a Joint Commission, Centers for Disease Control and Prevention (CDC), US Environmental Protection Agency (EPA), US Food and Drug Administration (FDA), Omics analytics, and any other organization or source of information related to patient diagnosis and care. In some embodiments, facility server 130 may receive best practice data from established best practice guidelines such as, for example, MCG or InterQual Criteria. In such embodiments, facility server 130 may receive best practice data from a database or data repository software, or from published health care guidelines.

In step 1408, facility server 130 may analyze the received and stored data. In some embodiments, facility server 130 may utilize one or more known statistical methods to evaluate hospital unit performance data against the best practice data and internal rule and policy data (step 1410). For example, facility server 130 may utilize one or more discrete simulation models such as Monte Carlo simulations, Brownian Motion models, distribution models, Bayesian statistics, SIPMath, T-tests, LEAN-SixSigma techniques, Fisher Exact tests, as well as other known or custom computer models, simulations, and data analysis techniques. Facility server 130 may access stored algorithms and computer model stored in database 180 or 470, or from another location accessed via network 150.

In step 1412, facility server may identify underperforming milestones and/or hospital units, to address inefficiency and inefficacies in the hospitals' protocols. For example, facility server 130 may determine that certain hospital units are consistently completing milestones late, and costing the hospital time and money via inefficiency. As another example, facility server 130 may determine that certain diagnosis related groups have relatively higher readmission rates when certain hospital protocols and itineraries are implemented, indicating that those protocols and itineraries are not effectively treating the patient(s). Facility server 130 may make these determinations, for example, using statistical analyses that identify outliers in datasets of patient readmission rates and length of stay metrics. Thus, facility server 130 may identify problems with hospital units and hospital procedures to continuously improve treatment efficiency and efficacy.

In step 1414, facility server 130 may determine whether the best practice data indicates an alternative milestone sequence that is consistent with more efficient hospital unit performance, such as a sequence of tests or treatment that has been proven in the hospital to be completed efficiently and resulted in effective patient treatment. Facility server 130 may evaluate multiple iterations and variations of milestone sequences and different hospital unit/milestone combinations. In some embodiments, facility server 130 may score and/or rank the combinations using a scoring or ranking system, to identify the most desirable combinations. Facility server 130 may then check the highest ranking combination(s) against the best practice data and hospital rules/policies, to ensure there are no conflicts with the hospitals internal procedures and rules, and that the combination(s) are consistent with known effective treatments for the diagnosis related group.

In step 1416, facility server 130 may create a new hospital protocol or refine an existing protocol, based on the results of the preceding steps.

In step 1418, facility server 130 may update a database such as database 180 or 470 with data entries corresponding to the newly created/refined hospital protocols. Thereafter, facility server may implement the new/refined protocols in subsequent patient itineraries, and the cycle depicted in FIG. 5 continues endlessly to improve hospital efficiency and patient treatment quality, by implementing real-time data collection using multiple types of computerized devices and sensors, as well as automating patient itinerary tasks using computer systems integrated within the hospital facilities.

Figure 15:
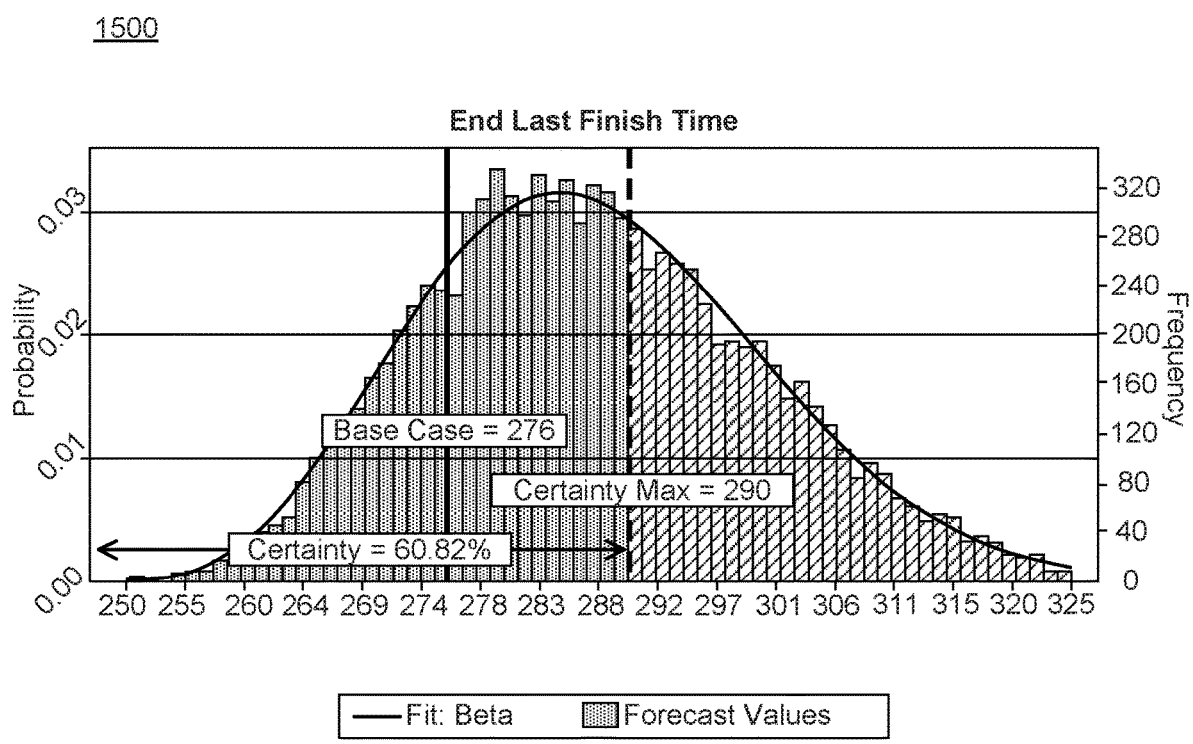
FIG. 15 is an illustration of an exemplary chart of a calculation for an End Last Finish Time or Estimated Length of Stay time range forecast, consistent with disclosed embodiments.

FIG. 15 is an illustration of a chart 1500 of a calculation for an End Last Finish Time or Estimated Length of Stay time range forecast given a prescribed confidence level. The End Last Finish Time may represent a forecasted value of the overall duration of a patient itinerary. For example, in FIG. 15 the End Last Finish Time may represent forecasted values for the length of stay. In some embodiments, FIG. 15 may be used for calculations of one or more other metrics associated with patient itineraries such as readmission rate, or fatality rate. The End Last Finish Time and Estimated Length of Stay time range forecast variable may influence the calculated Estimated Length of Stay, and facility server 130 may utilize these variables to determine an Estimated Length of Stay that is directly proportionate to these variables. Thus, chart 1500 represents possible values and variances around a metric associated with a patient itinerary, to provide a confidence level for the predicted value.

Chart 1500 is a visual representation of one or more analyses performed by facility server 130 which may occur during process 1200, 1300, or 1400. For example, analyses associated with chart 1500 may occur during step 1208, 1306, 1408, or 1410. In some embodiments, Chart 1500 may illustrate a distribution curve of forecasted values of key performance indicators (KPIs), to predict the forecasted value of a patient itinerary duration at a high confidence level such as 95%.

The example shown in FIG. 15 is a graphical depiction of a Monte Carlo simulation of durations for a In some embodiments, one or more processors other than facility server 130 may perform analyses associated with chart 1400 such as, for example, computer terminal 140, administrative terminal 145, user device 120, and any other processor in communication with network 150.

Chart 1500 illustrates a plot of historical patient itinerary durations in a unit of time such as minutes or hours, against an occurrence frequency of those durations. Chart 1500 may be used to plot the distribution of durations for a particular patient itinerary, accounting for variations in individual task durations and modifications to the itinerary. A sensitivity value may be determined to identify the tasks and values which are statistically significant. Based on the sensitivity value, facility server 130 may estimate a maximum estimated duration for the patient itinerary. As shown, facility server 130 may calculate a best-fit curve to the patient itinerary durations. In some embodiments, the best fit curve may be a bell curve. Facility server 130 may also calculate a reoccurrence probability for each duration. In some embodiments, facility server 130 may calculate a base case, and calculate a certainty max and a certainty percentage based for the base case. In some embodiments, the vase case may include a calculated value (in this case a duration for Last End Finish Time) based on a predefined subset of values, such as the average or median duration for each task in the patient itinerary. The certainty max value may represent the longest duration based on the determined sensitivity percentage value. Certainty max may also represent the result of the simulation model for a particular patient itinerary, after numerous iterations and taking into account distributions of each task in the patient itinerary. Sensitivity percentages may represent a statistical analysis of the tasks in the patient itinerary having the largest impact on the total duration of the patient itinerary. In the example shown, facility server 130 calculates a base case of 276, and determines that 290 is a maximum certain time, with a corresponding sensitivity percentage of 60.82%.

Figure 16:
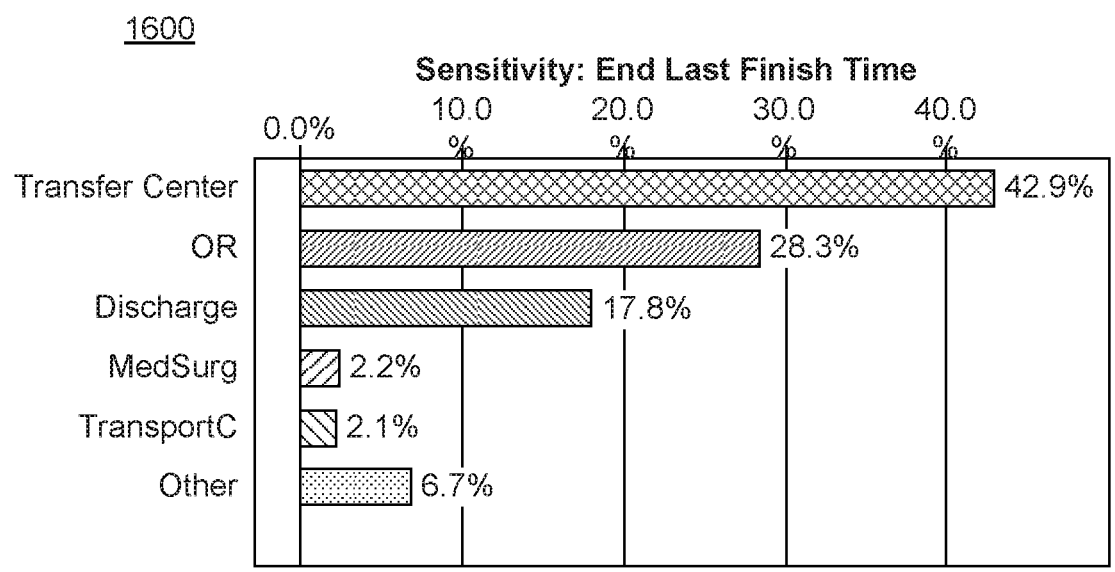
FIG. 16 is an illustration of an exemplary sensitivity chart for an End Last Finish Time or Estimated Length of Stay factors, consistent with disclosed embodiments.

FIG. 16 is a sensitivity chart 1600 showing calculations for task sensitivity values for an End Last Finish Time of a particular patient itinerary, consistent with disclosed embodiments. Chart 1600 includes sensitivity values for each task indicating an importance of each task in the calculation of the overall patient itinerary duration. In some embodiments, sensitivity may be determined based on variations in historical task completion times. In such embodiments, sensitivity may indicate tasks and milestones that are determined to have the highest variation over time. In some embodiments, sensitivity may be a numerical representation of the frequency that a particular task or function is on the critical path for certain patient itineraries. For example, a task or milestone that frequently appears in the critical path (as determined by hospital protocols or best practice guidelines) may be assigned a high sensitivity value, whereas a task or milestone that frequently appears as an optional task or milestone may be assigned a relatively lower sensitivity value. Thus, sensitivity may indicate an impact on the patient itinerary duration if a delay occurs in a particular task or milestone. Thus, delays in certain types of tasks or milestones may significantly delay patient discharge and lengthen the patient stay considerably. In contrast, milestones and tasks having lower sensitivities may not have a large impact on patient itinerary duration and length of stay if a statistically average delay occurs in low-sensitivity tasks and milestones.

Chart 1600 may represent backend calculations performed by facility server 130. In some embodiments, chart 1600 may represent calculations performed in connection with one or more steps of processes 1200, 1300, or 1400. For example, step 1412 of FIG. 14 may be associated with chart 1600. Chart 1600 may identify steps, milestones, tasks, or variables that have the greatest impact on the forecasted value (such as duration, efficiency, efficacy, etc.). In some embodiments, chart 1600 may indicate sensitivities associated with a value other than a performance metric for the patient itinerary such as, for example, a resource allocation. In the example shown, a transfer center task for admitting the patient and assigning a patient bed or the sum total of all transfer tasks for a given patient may have a sensitivity of 42.9%, indicating that the patient admission and placement tasks have the most significant impact on patient duration for this patient itinerary. Operating room tasks, such as surgery, may have sensitivity of 28.3%, as the second most impactful tasks in this patient itinerary. With a sensitivity of 17.8%, tasks related to patient discharge may have the next highest impact on patient itinerary duration. The medical surgical, transport, and other tasks may have a lower impact on the patient itinerary duration, and therefore have lower sensitivities.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

The invention claimed is:

1. A computerized system for automated routing in a facility, the system comprising:
at least one processor in communication with a communications network; and
a storage medium comprising instructions that, when executed, configure the at least one processor to:
receive health condition information of a single individual;
search a database in communication with the at least one processor to identify a set of multiple milestones associated with the health condition, wherein each milestone comprises a task of treatment for the single individual;
select, based on the set of milestones, a plurality of hospital units in the facility corresponding to hospital units for performing the set of milestones;
generate, within a patient itinerary creation and management application, an itinerary for the single individual from the set of multiple milestones and the plurality of hospital units, wherein the itinerary comprises aspects of care of the single individual for each of the multiple milestones within at least one of the plurality of hospital units;
receive, from the database, performance metrics of the plurality of hospital units, the performance metrics comprising historical and real-time performance data;
receive, from a third-party database, information related to patient diagnosis and care;
compile quantifiable efficiency or efficacy metrics for the plurality of hospital units from a plurality of devices, wherein the quantifiable efficiency or efficacy metrics are associated with operations of the plurality of hospital units and quality of care provided to patients within the plurality of hospital units, wherein at least one of the plurality of devices comprises a sensor device continuously providing metric data based on sensed conditions;
identify underperforming hospital units by comparing the quantifiable metrics with the information related to patient diagnosis and care;
determine the information related to patient diagnosis and care indicates an alternative sequence consistent with the facility procedures and that minimizes underperforming hospital units, wherein the alternative sequence is determined based on the health condition information, the set of multiple milestones, and the performance metrics by determining:
a sequence of the set of milestones,
an estimated completion time for each milestone based on historical turnaround times in combination with real-time status of corresponding hospital units,
a variation in historical completion times of each milestone within different hospital units, and a path through a set of hospital units for the alternative sequence based on the estimated completion times and variations, wherein the path is selected from a ranked combination of hospital units and corresponding historical completion time;

reduce delays in a stay of the patient by automatically recalculating and updating the itinerary based upon the determined path using the alternative sequence; and display, within the patient itinerary creation and management application, a graphical user interface illustrating the updated itinerary comprising the determined sequence and determined path, wherein the displaying comprises updating the graphical user interface as the patient progresses through the determined sequence and determined path, wherein the patient progress is identified using real-time tracking information of the patient.

2. The computerized system of claim 1, wherein the at least one processor is further configured to:

automatically generate and provide for communication an electronic message based on the determined sequence and path, wherein the generated electronic message is associated with a transportation request, a bed request, an equipment request, a caregiver presence request, or a lab request.

3. The computerized system of claim 2, wherein the generated electronic message causes an automated placement system operatively coupled to the patient itinerary creation and management application via the communications network to automatically reserve a bed for the patient.

4. The computerized system of claim 1, wherein the at least one processor is further configured to:

receive a progress status of a milestone in the set of milestones from sensors located throughout the facility;

determine, from the progress status, whether the milestone's duration differs from the corresponding estimated completion time by at least a standard deviation;

automatically revise the sequence and the path when the milestone duration differs from the corresponding estimated completion time by cancelling one or more milestones in the set of milestones; and automatically generate at least one electronic message comprising the revised sequence and the revised path, and instructions to modify the graphical user interface.

5. The computerized system of claim 1, wherein the at least one processor is further configured to receive real-time location data of a sensor device associated with the single individual, and the path is determined in part based on a proximity of the sensor device to the plurality of hospital units.

6. A computerized method for automated routing in a facility comprising:

receiving, by at least one processor, health condition information of a single individual;

searching a database in communication with the at least one processor to identify health condition information, wherein each milestone comprises a task of treatment for the single individual;

selecting, based on the set of milestones, a plurality of hospital units in the facility corresponding hospital units for performing the set of milestones;

generating, within a patient itinerary creation and management application, an itinerary for the single individual from the set of multiple milestones and the plurality of hospital units, wherein the itinerary comprises aspects of care of the single individual for each of the multiple milestones within at least one of the plurality of hospital units;

receiving, by the at least one processor from the database, performance metrics of the plurality of hospital units, the performance metrics comprising historical and real-time performance data;

receiving, from a third-party database, information related to patient diagnosis and care;

compiling quantifiable efficiency or efficacy metrics for the plurality of hospital units from a plurality of devices, wherein the quantifiable efficiency or efficacy metrics are associated with operations of the plurality of hospital units and quality of care provided to patients within the plurality of hospital units, wherein at least one of the plurality of devices comprises a sensor device continuously providing metric data based on sensed conditions;

identifying underperforming hospital units by comparing the quantifiable metrics with the information related to patient diagnosis and care;

determining the information related to patient diagnosis and care indicates an alternative sequence consistent with the facility procedures and that minimizes underperforming hospital units, wherein the alternative sequence is determined based on the health condition information, the set of multiple milestones, and the performance metrics by determining:

a sequence of the set of milestones, an estimated completion time for each milestone based on historical turnaround times in combination with real-time status of corresponding hospital units, a variation in historical completion times of each milestone within different hospital units, and a path through a set of hospital units for the alternative sequence based on the estimated completion times and variations, wherein the path is selected from a ranked combination of hospital units and corresponding historical completion time;

reducing delays in a stay of the patient by automatically recalculating and updating the itinerary based upon the determined path using the alternative sequence; and displaying, within the patient itinerary creation and management application, a graphical user interface illustrating the updated itinerary comprising the determined sequence and determined path, wherein the displaying comprises updating the graphical user interface as the patient progresses through the determined sequence and determined path, wherein the patient progress is identified using real-time tracking information of the patient.

7. The computerized system of claim 6, further comprising:

automatically generating and providing for communication an electronic message based on the determined sequence and path, wherein the generated electronic message is associated with a transportation request, a bed request, an equipment request, a caregiver presence request, or a lab request.

8. The computerized system of claim 7, wherein the generated electronic message causes an automated placement system operatively coupled to the patient itinerary creation and management application via a communications network to automatically reserve a bed for the patient.

9. The computerized system of claim 6, further comprising:
receiving a progress status of a milestone in the set of milestones from sensors located throughout the facility;
determining, from the progress status, whether the milestone's duration differs from the corresponding estimated completion time by at least a standard deviation;
automatically revising the sequence and the path when the milestone duration differs from the corresponding estimated completion time by cancelling one or more milestones in the set of milestones; and
automatically generating at least one electronic message associated with the revised sequence and the revised path, and instructions to modify the graphical user interface.

10. The computerized system of claim 6, further comprising:
receiving real-time location data of a sensor device associated with the individual, wherein the path is determined in part based on a proximity of the sensor device to the plurality of hospital units.

11. A non-transitory computer-readable medium storing instructions which, when executed, cause one or more processor to perform a computerized method for automated routing in a facility, comprising:
receiving, by at least one processor, health condition information of a single individual;
searching a database in communication with the at least one processor to identify health condition information, wherein each milestone comprises a task of treatment for the single individual;
selecting, based on the set of milestones, a plurality of hospital units in the facility corresponding hospital units for performing the set of milestones;
generating, within a patient itinerary creation and management application, an itinerary for the single individual from the set of multiple milestones and the plurality of hospital units, wherein the itinerary comprises aspects of care of the single individual for each of the multiple milestones within at least one of the plurality of hospital units;
receiving, by the at least one processor from the database, performance metrics of the plurality of hospital units, the performance metrics comprising historical and real-time performance data;
receiving, from a third-party database, information related to patient diagnosis and care;
compiling quantifiable efficiency or efficacy metrics for the plurality of hospital units from a plurality of devices, wherein the quantifiable efficiency or efficacy metrics are associated with operations of the plurality of hospital units and quality of care provided to patients within the plurality of hospital units, wherein at least one of the plurality of devices comprises a sensor device continuously providing metric data based on sensed conditions;
identifying underperforming hospital units by comparing the quantifiable metrics with the information related to patient diagnosis and care;
determining the information related to patient diagnosis and care indicates an alternative sequence consistent with the facility procedures and that minimizes underperforming hospital units, wherein the alternative sequence is determined based on the health condition information, the set of multiple milestones, and the performance metrics by determining:
a sequence of the set of milestones,
an estimated completion time for each milestone based on historical turnaround times in combination with real-time status of corresponding hospital units,
a variation in historical completion times of each milestone within different hospital units, and
a path through a set of hospital units for the alternative sequence based on the estimated completion times and variations, wherein the path is selected from a ranked combination of hospital units and corresponding historical completion time;
reducing delays in a stay of the patient by automatically recalculating and updating the itinerary based upon the determined path using the alternative sequence; and
displaying, within the patient itinerary creation and management application, a graphical user interface illustrating the updated itinerary comprising the determined sequence and determined path, wherein the displaying comprises updating the graphical user interface as the patient progresses through the determined sequence and determined path, wherein the patient progress is identified using real-time tracking information of the patient.

12. The computerized method of claim 11, further comprising:
automatically generating and providing for communication an electronic message based on the determined sequence and path, wherein the generated electronic message is associated with a transportation request, a bed request, an equipment request, a caregiver presence request, or a lab request.

13. The computerized method of claim 12, wherein the generated electronic message causes an automated placement system operatively coupled to the patient itinerary creation and management application via a communications network to automatically reserve a bed for the patient.

14. The computerized method of claim 11, further comprising:
receiving a progress status of a milestone in the set of milestones from sensors located throughout the facility;
determining, from the progress status, whether the milestone's duration differs from the corresponding estimated completion time by at least a standard deviation;
automatically revising the sequence and the path when the milestone duration differs from the corresponding estimated completion time by cancelling one or more milestones in the set of milestones; and
automatically generating at least one electronic message associated with the revised sequence and the revised path, and instructions to modify the graphical user interface.

15. The computerized method of claim 11, further comprising:
receiving real-time location data of a sensor device associated with the individual, wherein the path is determined in part based on a proximity of the sensor device to the plurality of hospital units.

16. The computerized system of claim 1, wherein the graphical user interface comprises a flowchart comprising:
a plurality of light boxes associated with milestones in the sequence of milestones that are pending or that were completed;
a plurality of shaded boxes associated with milestones that are not required to complete a treatment for the single individual; and
a plurality of arrows connecting light and shaded boxes according to the determined path, wherein light and shaded boxes provide information about the corresponding milestone including at least one of: an average wait time, a key performance indicator, a completion percentage, or a delay time.

17. The computerized system of claim 16, wherein the graphical user interface further comprises a table displaying:
   one row for each milestone in the sequence of milestones; and
   a plurality of columns displaying monitoring values associated with each milestone, the monitoring values comprising a dependency, a lead lag time, an optimistic duration, an expected duration, an earliest start time, an earliest finish time, a latest start time, a latest finish time, and a probability value that the milestone is on a Critical Path of care.

18. The computerized system of claim 16, wherein the at least one processor is further configured to:
   generate, for display, a second graphical user interface when a user interacts with one of the light or shaded boxes, the second graphical user interface comprising additional metrics and options for modifying a selected milestone.

19. The computerized system of claim 4, wherein the at least one processor is further configured to:
   identify an alternative sequence of milestones when determining a user has manually indicated a delay or complication with one of the milestones in the sequence; and
   generate a request for caregiver authorization to update the sequence.

* * * * *